United States Patent [19]

Kirchhoff

[11] Patent Number: 5,026,892

[45] Date of Patent: Jun. 25, 1991

[54] POLY(ARYLCYCLOBUTENES)

[75] Inventor: Robert A. Kirchhoff, Midland, Mich.

[73] Assignee: The Dow Chemical Company, Midland, Mich.

[21] Appl. No.: 360,665

[22] Filed: Jun. 2, 1989

Related U.S. Application Data

[60] Division of Ser. No. 883,240, Jul. 8, 1986, abandoned, which is a continuation-in-part of Ser. No. 644,836, Aug. 27, 1984, abandoned.

[51] Int. Cl.$^5$ ............................................. C07F 7/10
[52] U.S. Cl. ............................. 556/419; C07F/7/10
[58] Field of Search ........................................ 556/419

[56] References Cited

U.S. PATENT DOCUMENTS

| | | | |
|---|---|---|---|
| 4,540,763 | 9/1985 | Kirchhoff | 526/281 |
| 4,622,375 | 11/1986 | Wong | 526/284 |
| 4,638,078 | 1/1987 | Kirchhoff | 558/414 |
| 4,642,329 | 2/1987 | Kirchhoff et al. | 526/284 |
| 4,661,193 | 4/1987 | Kirchhoff et al. | 156/307.3 |
| 4,667,004 | 5/1987 | Wong | 526/284 |
| 4,667,005 | 5/1987 | Wong | 526/284 |
| 4,675,370 | 6/1987 | Tan et al. | 526/259 |
| 4,687,823 | 8/1987 | Kirchhoff et al. | 526/284 |
| 4,708,994 | 11/1987 | Wong | 525/392 |
| 4,711,964 | 12/1987 | Tan et al. | 548/461 |
| 4,724,260 | 2/1988 | Kirchhoff et al. | 546/112 |
| 4,759,874 | 7/1988 | Gros | 256/512 |
| 4,795,827 | 1/1989 | Bruza et al. | 564/329 |
| 4,812,588 | 3/1989 | Schrock | 556/453 |
| 4,831,172 | 5/1989 | Habu et al. | 556/419 |

FOREIGN PATENT DOCUMENTS

0193721  1/1986  European Pat. Off. ............ 556/419

OTHER PUBLICATIONS

Perkins et al., *Agnew Chem. Int. Ed. Engl.*, 17(8), 615(1978).
Ewing et al., *J.C.S. Chem Comm.*, 207(1979).
Boekelheide et al., *Tetrahedron Letters*, 4245(1978).
Cava et al., *JACS*, 81 4266(1959).
Gray et al., *JACS*, 100,2892(1978).
Gray et al., *JACS*, 100(9), 2893(1978).
Hubert et al., *J. Chem. Soc.*, 3160(1960).
Stille, *Fortschr. Hochpolym. Forsch.* Bd. 3,S.34(1961).
Schiess, *Tetrahedron Letters*, (46)4569(1978).
Klundt, *Chem. Rev.*, 70(4), 471(1970).
Errede, *JACS*, 83,949(1961).
Louden et al., *JACS*, 91(27), 7577(1969).
Flynn et al., *JACS*, 96(10), 3280(1974).
Spangler et al., *Tetrahedron Letters*, (29)2517(1976).
Loon-Sent Tan et al., *Polymer Preprints*, 27(2), 240(1986).
Loon-Seng Tan, *Polymer Preprints*, 26(2), 176, 178 (1985).
Loon-Seng Tan, *Polymer Preprints*, 27(1), 453(1986).
Loon-Seng Tan, preprint from the Spring 1987, ASC Polymeric Materials Science and Engineering Conference.
Denny et al., "Characterization of a Bisbenzocyclobutene High Temperature Resin and a Benzocyclobutene Blended with a Compatible Bismaleimide Resin", *Polymer Material Science Engineering*, 56, pp. 656–659, (1987).
Denny et al., "High Temperature Bisbenzocyclobutene Terminated Resin Properties", *Polymer Preparations*, 29(1), pp. 194–195.

*Primary Examiner*—Paul F. Shaver

[57] ABSTRACT

The invention is a poly(arylcyclobutene) comprising arylcyclobutene moieties connected by a bridging member, wherein the bridging member comprises an amidoalkyl termintated polysiloxane, and wherein one or more cyclobutene rings are fused to one of the aryl rings.

8 Claims, No Drawings

NOVEL POLY(ARYLCYCLOBUTENES)

CROSS-REFERENCE TO RELATED APPLICATIONS

This Application is a divisional of co-pending application Ser. No. 883,240, filed Jul. 8, 1986, now abandoned (incorporated herein by reference) which is a continuation-in-part of co-pending application Ser. No. 644,836, filed Aug. 27, 1984, now abandoned (incorporated herein by reference).

BACKGROUND OF THE INVENTION

The invention relates to novel poly(arylcyclobutene) monomers.

The poly(arylcyclobutene) monomers of this invention are useful in the preparation of a wide range of polymeric compositions. These polymeric compositions are useful in films, as molded articles, in coatings, as adhesives, and in composites.

In recent years the search for high-performance materials, especially high-temperature-resistance polymers, has gained momentum. In order for a material to be useful at high temperatures, it must fulfill several requirements including a high melting or softening temperature, a high modulus or rigidity at elevated temperature, a resistance to solvent and chemical degradation, and toughness. The intrinsic thermal and oxidative stability of aromatic structures has long been recognized, and a variety of polymers have been made in which benzene rings are linked together by various connecting groups. Among the more stable aromatic polymers that fulfill the requirements of high-temperature resistance are the polybenzimidazoles, the polybenzoxazoles, polyimides, and some polyamides, such as the polyaramides. Of these polymers, the polyimides have had the most interest.

The major difficulty encountered in the commercial development of these materials is that they are usually obtained in the form of a powder which cannot be readily fabricated into useful objects.

The polyimides prepared from aliphatic diamines and aromatic dianhydrides are generally soluble and thermoplastic. Aliphatic polyimides have been prepared from bis(dienophiles) and a diene such as a bisdiene. In many cases, such reactions proceed with the evolution of gases and other volatile components.

Aromatic polyimides, such as polypyromellitimides, have a spectrum of superior properties. These polyimides may be prepared by the reaction of an aromatic dianhydride with an aromatic diamine to give a soluble polyamic acid, which on cyclodehydration gives the insoluble desired product.

High performance plastics reduce the weight of mechanical components, and not just by virtue of their densities. Their high performance properties allow greater design stresses, and often elements can be downsized accordingly. In recent years, aromatic polyimides have become widely accepted as premium, high performance engineering plastics. These resins are well-known for having excellent properties at elevated temperatures (i.e., chemical resistance and mechanical strength) but are also costly. Historically, polyimide resins are difficult to fabricate into objects other than fibers and films. The most common methods of manufacturing parts having high strength and temperature properties are hot compression-molding, machining from hot-compression, and molded or extruded rod.

Given the synthetic and fabrication difficulties, a new route to polyimides and other high performance plastics is desirable.

Many monomers used heretofore to prepare thermally polymerizable compounds have a poor shelf-life and are unstable in the presence of oxygen or oxygen-containing gases. Further, many processes for the polymerization of thermally polymerizable compounds result in the generation of volatile components, which can create problems in the product such as the creation of voids in molded articles. Further, the removal of such volatile by-products can create problems. Also, many of such polymerization processes require the use of curing agents, initiators or catalysts. The use of such curing agents, initiators or catalysts often result in polymers which contain impurities which may effect the final properties.

Monomers which can undergo polymerization through thermal mechanisms; which do not require the use of catalysts, initiators or curing agents; and which do not form volatile by-products are needed. Monomers which polymerize by thermal mechanisms, which have a good stability, shelf-life, and are stable in the presence of oxygen are desirable. Monomers which form polymers by thermal polymerization mechanisms, with a good modulus, which are thermally stable, which have low water pickup, are reasonably hard and are insoluble are needed.

SUMMARY OF THE INVENTION

The invention is poly(arylcyclobutenes) comprising aryl moieties with one or more cyclobutene rings fused to each aryl moiety, wherein the aryl moieties are directly bonded to one another or are connected by a bridging member wherein the bridging member is (1) a polyvalent inorganic radical or (2) a polyvalent organic radical which (a) contains one or more heteroatoms comprising oxygen, sulfur, nitrogen, silicon or phosphorus, or (b) one or more aromatic radicals. Preferably, each aryl moiety is bonded by a single direct bond to another aryl moiety, or a single bond to a bridging member.

The novel compounds of this invention are useful in the preparation of polymeric compositions. Such polymeric compositions can be prepared by heating the monomers to a temperature at which such monomers polymerize. These monomers upon heating to the appropriate temperature undergo a polymerization in which no volatiles are generated, wherein there is no need for a catalyst, curing agent or initiator. These monomers have a surprisingly good shelf-life and stability to oxygen-containing gases. The polymers prepared have a good modulus, are thermally stable, have a low water pickup, are reasonably hard and insoluble.

DETAILED DESCRIPTION OF THE INVENTION

This invention relates to poly(arylcyclobutenes), wherein poly(arylcyclobutenes) refers herein to a compound containing 2 or more arylcyclobutene moieties connected either by a direct bond or bridging member. An arylcyclobutene moiety refers herein to an aryl group which contains one or more cyclobutene rings fused to at least one of the aromatic rings. Aryl refers herein to any aromatic moiety. Aromatic as used herein refers to carbocyclic or heterocyclic rings in which $4n+2$ delocalized $\pi$ elections are contained in an orbital ring. This property is also known as resonance stabilization or delocalization. Preferred carbocyclic aromatic moieties include benzene, naphthalene, phenanthrene, anthracene, a biaryl moiety, or 2 or more aromatic radicals bridged by alkylene or cycloalkylene moieties. More preferred carbocyclic aromatic radicals are benzene, naphthalene, biphenyl, binaphthyl, diphenyl alkane or diphenyl cycloalkane radicals. The most preferred carbocyclic aromatic radical is a benzene radical. Examples of preferred heterocyclic aromatic compounds include pyrrole, furan, thiophene, imidazole, oxazole, thiazole, pyrazole, pyridine, and pyrimidine. More preferred heterocyclic aromatic compounds are pyridine, furan, and thiophene, with pyridine being most preferred. The carbocyclic aromatic rings are preferred over the heterocyclic aromatic rings.

The aryl radical and cyclobutene ring may be substituted with a variety of substituents. Such substituents may be electron-donating or electron-withdrawing groups. Examples of such substituents include cyano, halo, carboxy, hydrocarbyloxy, carbonyl, alkanoyl, aroyl, alkylsulfonyl, alkylsulfonoyl, amino, amido, or aryl groups.

The arylcyclobutene moieties are connected herein by a direct bond or bridging member. Bridging members comprise (1) a polyvalent inorganic moiety, or (2) a polyvalent organic moiety containing (a) one or more heteroatoms, comprising O, P, N, Si, or S, or (b) one or more aromatic radicals. The bridging member or direct bond connects the arylcyclobutene moieties through the aryl radical.

Polyvalent inorganic moiety refers to any inorganic moiety which is capable of bonding to 2 or more aryl radicals. Such polyvalent inorganic moieties can be covalently or ionically bonded to the aromatic radical. Examples of polyvalent inorganic moieties include oxygen, phosphorus, silicon, phosphorus oxide, sulfur, nitrogen, polysiloxanes, polyvalent metals, sulfoxide, sulfone, a polyvalent metal bound to a polyvalent oxygenated moiety wherein the polyvalent oxygenated moiety can be further bound to an aryl radical (for example, a polyvalent carboxylate salt). Preferred polyvalent inorganic moieties include oxygen, sulfur, silicon, polysiloxanes, and polyvalent metals bound to polyvalent oxygenated moieties.

The polyvalent organic bridging member can be any polyvalent organic moiety containing one or more heteroatoms, comprising oxygen, nitrogen, phosphorus, silicon, or sulfur, or an organic moiety containing one or more aromatic radicals, which can link 2 or more aryl radicals. Preferably, the polyvalent organic bridging member is a hydrocarbon poly-yl which is bonded to functionalized linking groups or a hydrocarbon poly-yl which contains an aromatic radical. Hydrocarbon poly-yl is a hydrocarbon moiety which is bonded to 2 or more linking groups, wherein the hydrocarbon poly-yl may further contain one or more of the hereinbefore defined heteroatoms. Included within the term hydrocarbon are any organic radicals containing carbon and hydrogen atoms. Hydrocarbons include the following organic radicals: alkanes, alkenes, alkynes, cycloalkanes, cycloalkenes, carbocyclic aromatic radicals, wherein aromatic is as defined hereinbefore, alkyl-substituted aromatic radicals, and aryl-substituted aliphatic radicals.

Linking group refers herein to any group which is capable of linking a hydrocarbon radical to an aryl radical. Linking groups include oxygen, sulfur, sulfoxide, sulfone, nitrogen, phosphorus, silicon, phosphorus oxide, carbonyloxy, amido, carbonyl, carbonyldioxy, cyclic amido, carboxamidooxy, ureylene, carbonyloxycarbonyl, ammonium carboxylate salt and imido. Preferred linking groups are oxygen, sulfur, nitrogen, carbonyloxy, amido, carbonyldioxy, or cyclic amido. More preferred linking groups are carbonyloxy and amido.

Preferably the arylcyclobutene moieties are connected by direct bond or polyvalent organic moieties containing (1) one or more heteroatoms or (2) one or more aromatic radicals. Most preferably, the arylcyclobutene moieties are connected by the bridging members comprising the polyvalent organic moieties containing (1) one or more heteroatoms or (2) one or more aromatic radicals.

In one preferred embodiment, the polyvalent bridging member is a divalent bridging member. More preferred divalent bridging members include dicarbonyloxy hydrocarbylene, dicarboxamido hydrocarbylene, dicarbonyldioxy hydrocarbylene, dioxyhydrocarbylene, dithiohydrocarbylene or an aromatic radical-containing hydrocarbylene group.

Even more preferred divalent organic bridging members are dicarbonyloxyhydrocarbylene, dicarboxamidohydrocarbylene, di(carbonyloxy)hydrocarbylene, dioxyhydrocarbylene, dithiohydrocarbylene, and an aromatic radical-containing hydrocarbylene group.

Examples of polyvalent organic bridging members include the following: polyoxy(alk-poly-yl), polyoxy(ar-poly-yl), polyoxy(alkar-poly-yl), polyoxy (aralk-poly-yl), polythio(alk-poly-yl), polythio(ar-poly-yl), polythio(alkar-poly-yl), polythio(aralk-poly-yl), polyamido(alk-poly-yl), polyamido(ar-poly-yl), polyamido-(alkar-poly-yl), polyamido(aralk-poly-yl), polycarbonyloxy(alk-poly-yl), polycarbonyloxy(ar-poly-yl), polycarbonyloxy(alkar-poly-yl), polycarbonyloxy(aralk-poly-yl, polycarbonyldioxy(alk-poly-yl), polycarbonyldioxy(ar-poly-yl), polycarbonyldioxy-(alkar-poly-yl), polycarbonyldioxy(aralk-poly-yl), polyamino(alk-poly-yl), polyamino(ar-poly-yl), polyamino(alkar-poly-yl), polyamino-(aralk-poly-yl), polycyclicimido(ar-poly-yl), polycyclicimido(alkar-poly-yl), polycyclicimido(aralk-poly-yl), polycarbonyl-(alk-poly-yl), polycarbonyl(ar-poly-yl), polycarbonyl(alkar-poly-yl), polycarbonyl(aralk-poly-yl), polyimido(alk-poly-yl), polyimido(ar-poly-yl), polyimido(alkar-poly-yl), polyimido(aralk-poly-yl), polyureylene(alk-poly-yl), polyureylene(ar-poly-yl), polyureylene(alkar-poly-yl), polyureylene(aralk-poly-yl), polycarboxamideoxy(alk-poly-yl), polycarboxamideoxy(ar-poly-yl), polycarboxamideoxy(alkar-poly-yl), polycarboxamideoxy(aralk-poly-yl), ar-poly-yl, alkaryl-poly-yl, aralkyl-poly-yl, and alkenoic-poly-yl.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenyl, phenyl, naphthyl, phenanthrenyl, anthracenyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylene refers herein to a divalent hydrocarbon radical. Poly-yl refers herein to a polyvalent radical, for example, ar-poly-yl refers to a polyvalent aromatic radical. Poly refers herein to two or more.

Preferred poly(arylcyclobutenes) correspond to the formula

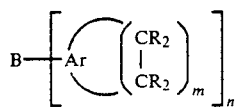
I wherein B is a direct bond or bridging member which comprises (1) a polyvalent inorganic radical, or (2) a polyvalent organic radical containing (a) one or more heteroatoms comprising oxygen, sulfur, nitrogen, silicon, or phosphorus, or (b) one or more aromatic radicals; Ar is an aromatic radical which may be substituted; R is separately in each occurrence hydrogen or an electron-withdrawing or electron-donating substituent; m is an integer of 1 or more; and n is an integer of 2 or more, with the proviso that B can only be a direct bond wherein n is 2.

In one preferred embodiment, the aromatic radical is benzene and m is 1. In this preferred embodiment, the poly(arylcyclobutenes) can be referred to as poly(benzocyclobutenes). Preferred poly(benzocyclobutenes) correspond to the formula

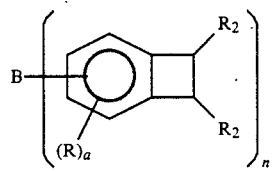
II wherein a is 3, and B, R, and n are as defined hereinbefore. R is preferably hydrogen, a cyano, or hydrocarbyloxycarbonyl group; more preferably hydrogen or cyano; and most preferably hydrogen.

In one embodiment, B can be polyvalent inorganic bridging member, wherein inorganic bridging member is as defined hereinbefore. Preferably inorganic polyvalent moieties include -O-, -S-,

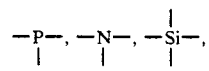

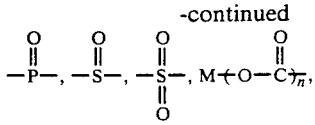

n valent M,

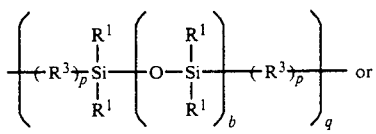

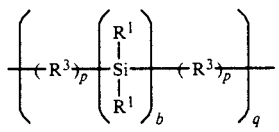

wherein M is a metal; $R^1$ separately in each occurrence an alkyl, aryl, alkaryl, aralkyl, alkoxy, aryloxy, alkaryloxy or aralkyloxy, wherein $R^3$ is separately in each occurrence alkylene, cycloalkylene, or alkenylene; an b is an integer of 1 or greater. p is separately in each occurrence 0 or 1. q is 1 or greater, preferably 1 to 20, more preferably 1 to 10, and most preferably 1 to 3. More preferably polyvalent inorganic bridging members include -O-, -S-, -N-,

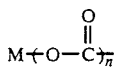

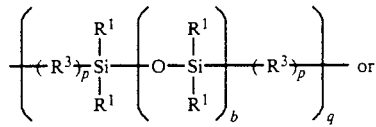

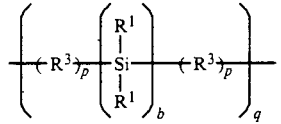

Even more preferred polyvalent inorganic bridging members include

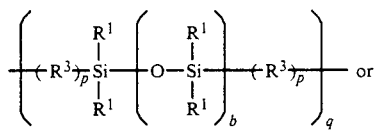

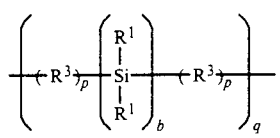

Most preferred polyvalent inorganic bridging members include

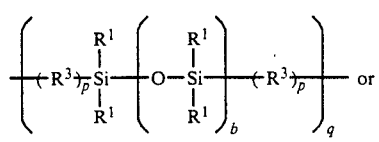

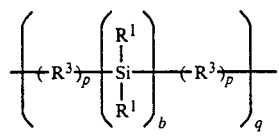

R$^1$ is preferably C$_{1-20}$ alkyl, C$_{6-20}$ aryl, C$_{7-20}$ alkaryl, C$_{7-20}$ aralkyl, C$_{1-20}$ alkoxy, C$_{6-20}$ aryloxy, C$_{7-20}$ alkaryloxy, or C$_{7-20}$ aralkyloxy. R$^1$ is more preferably C$_{1-20}$ alkyl or C$_{1-20}$ alkoxy, even more preferably C$_{1-10}$ alkyl, C$_{1-10}$ alkoxy, and most preferably C$_{1-4}$ alkyl or C$_{1-4}$ alkoxy.

Polyvalent organic radical is as defined hereinbefore. Preferred polyvalent organic radicals include those wherein B is (a) the formula X—Z—$_n$ wherein X is a hydrocarbon poly-yl radical wherein the hydrocarbon poly-yl can contain a heteroatom of oxygen, phosphorus, sulfur or nitrogen, and Z is a functionalized linking moiety; or (b) a hydrocarbon poly-yl containing one or more aromatic moieties. Hydrocarbon poly-yl is as defined hereinbefore. The functionalized linking moiety is as defined hereinbefore. Preferably, X is an alk-poly-yl, cycloalk-poly-yl, ar-poly-yl, alkar-poly-yl, a biaromatic alkylene or cycloalkylene bridged poly-yl. More preferably, X is —(CH$_2$)$_p$—,

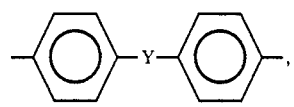

a phenylene, biphenylene, or cycloalkylene wherein Y is a C$_{1-20}$ straight- or branched-chain radical or a cycloalkylene radical and p is an integer of between about 2 and 20, inclusive. Most preferably X is —(CH$_2$)$_p$—, phenylene,

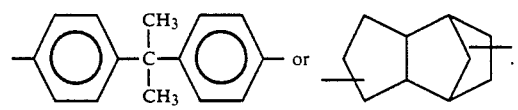

Preferably, Z is O, S, N, P, Si,

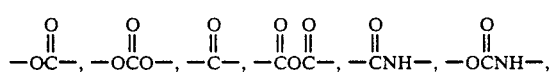

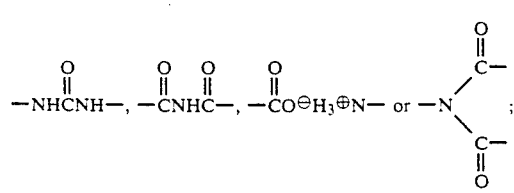

more preferably O, S,

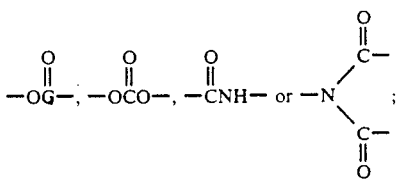

and most preferably

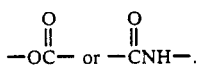

Preferred poly(benzocyclobutene) monomers include those with carboxamide-linking groups wherein the bridging members correspond to the formulas

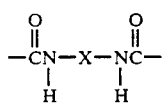

and

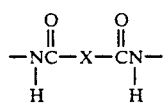

those with carbonyloxy-linking groups wherein the bridging members correspond to the formulas

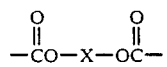

and

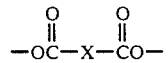

those with carbonyldioxy-linking groups wherein the bridging member corresponds to the formula

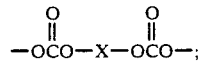

those with oxygen-linking groups wherein the bridging member corresponds to the formula

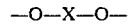

those with sulfur-linking groups wherein the bridging member corresponds to the formula

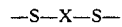

and those with cyclic imid-linking groups wherein the bridging member corresponds to the formula

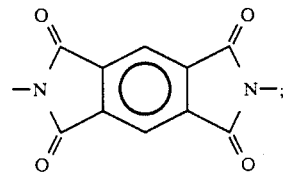

wherein X is as hereinbefore defined. More preferred bridging members which contain carboxamide-linking groups correspond to the following formulas:

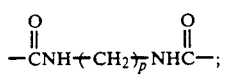

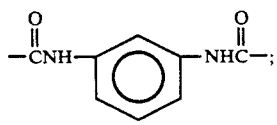

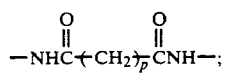

and

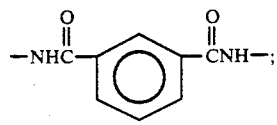

wherein p is as defined hereinbefore and p is an integer of 1 or greater, preferably between 1 and 20. More preferred bridging members with carbonyloxy-linking groups correspond to the formulas:

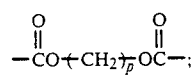

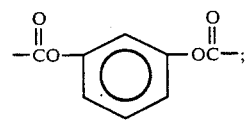

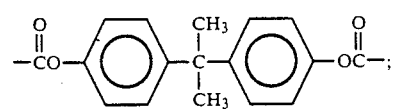

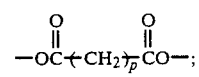

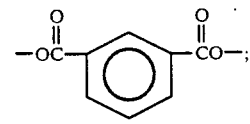

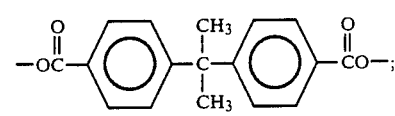

and

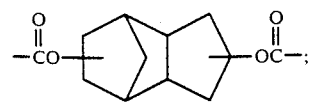

wherein p is as defined hereinbefore. More preferred bridging members wherein the linking group is carbonyldioxy include those which correspond to the following formulas

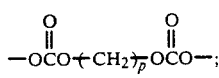

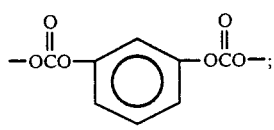

and

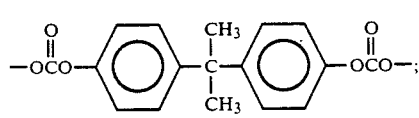

wherein p is as defined hereinbefore. More preferred bridging members with oxygen-linking groups include those which correspond to the formulas

and

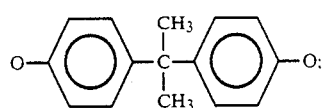

wherein p is as defined hereinbefore. More preferred bridging members with sulfur-linking groups include those which correspond to the formula

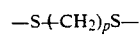

wherein p is as defined hereinbefore. More preferred bridging members with cyclic imid-linking groups include those which correspond to the formula

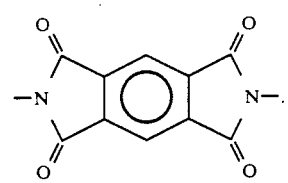

In one preferred embodiment, the polyvalent organic bridging member contains one or more aromatic radicals, and such bridging member generally corresponds to the formula

wherein Ar is as hereinbefore defined; $R^3$ is separately in each occurrence an alkylene, cycloalkylene or alkenylene radical; r is independently in each occurrence 0 or 1; and q is 1 or greater. $R^3$ is preferably a $C_{1-20}$ alkylene or $C_{1-20}$ alkenylene. $R^3$ is more preferably $C_{1-10}$ alkylene or $C_{1-10}$ alkenylene. $R^3$ is even more preferably $C_{1-4}$ alkylene or $C_{1-4}$ alkenylene, with —CH=CH— being most preferred. Preferably q is between 1 and 20, most preferably between 1 and 10. In a more preferred embodiment, the aromatic radical hydrocarbon poly-yl bridging member corresponds to the formula

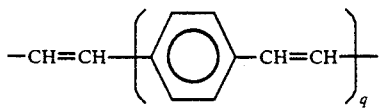

wherein q is as hereinbefore defined.

The poly(arylcyclobutene) monomers of this invention can be prepared by several synthesis schemes. The preferred methods of preparation of such monomers are described hereinafter.

In one synthesis scheme, an alkyl-substituted aromatic compound which is further substituted with an aryl deactivating substituent is chloroalkylated in a position ortho to the alkyl group. In the preferred embodiment wherein the aromatic compound is benzene, the starting material corresponds to the following formula

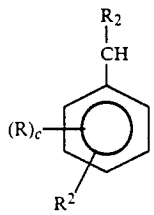

wherein R is as defined hereinbefore; $R^2$ is any aryl deactivating substituent; and c is an integer of 0, 1, 2, or 3. The alkyl-substituted aromatic compound is chloroalkylated by contacting the alkyl aromatic compound with a chloroalkylating agent and thionyl chloride in the presence of an iron chloride catalyst so as to result in a product which contains a chloroalkyl group ortho to the alkyl substituent. In the embodiment wherein the aromatic compound is a benzene ring, the product corresponds to the formula

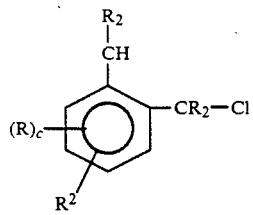

wherein R is as defined hereinbefore and $R^2$ is an aryl deactivating group. $R^2$ is preferably a hydrocarbyloxycarbonyl, carboxamide, hydrocarbylcarbonyl, carboxylate, halocarbonyl, nitrile, nitro, sulfone or sulfoxide group. $R^2$ is more preferably a halo or hydrocarbyloxycarbonyl group, with hydrocarbyloxycarbonyl being the most preferred group. Preferably c is 0 or 1, most preferably 0.

In this process the chloroalkylating agent is preferably chloromethyl methyl ether, although other chloroalkylating agents such as bis(chloromethyl) ether could be used. At least a 2:1 molar excess of the chloroalkylating agent to the alkyl-substituted aromatic compound is needed. It is preferable to use at least about a 3:1 ratio of chloroalkylating agent to alkyl aromatic compound. The catalyst is ferric chloride ($FeCl_3$) while the cocatalyst is thionyl chloride. The catalyst can be present in between about 0.05 and 1.0 mole per mole of alkyl aromatic. More preferably between about 0.1 and 0.4 mole of catalyst are present for each mole of alkyl aromatic compound. Preferably between about 0.05 and 1.0 mole of thionyl chloride per mole of alkyl aromatic is used, more preferably between about 0.1 and 0.4 mole per mole of alkyl aromatic.

This process can be performed at a temperature of between about 40° C. and 80° C., preferably about 40° C. and 60° C. Below about 40° C., the reaction rate is low. The boiling point of some of the components of the reaction mixture starts at about 60° C.

This process can be performed by contacting the alkyl aromatic compound with the chloroalkylating agent, catalyst and cocatalyst in a suitable solvent. Suitable solvents include chlorinated hydrocarbon solvents. Thereafter the reaction mixture is heated to the appropriate temperature. The product can be recovered by quenching the reaction mixture with alcohols or water to inactivate the chloroalkylating agents remaining, stripping off the volatiles and washing out the catalyst with water. The product thereafter is recovered by distillation.

The ortho chloroalkylated alkyl aromatic compounds can be converted to aromatic compounds with cyclobutene rings fused thereto, by pyrolysis. This is achieved by contacting the ortho chloroalkylated alkyl aromatic compound with at least 2 times its weight of a suitable diluent, and thereafter passing the mixture through a reactor at a temperature of 550° C. or greater and a pressure of between about atmospheric and 25 mm of mercury. Suitable diluents are generally substituted aromatic compounds which are inert to the chloroalkylated alkyl aromatic compound and are stable at pyrolysis temperatures. Examples of suitable diluents are benzene, toluene, xylenes, chlorobenzenes, nitrobenzenes, methylbenzoates, phenyl acetate or diphenyl acetate. Preferred diluents are the xylenes. Preferable temperatures are between about 700° C. and 750° C.. Preferable pressures are between about 35 and 25 mm of mercury. In a preferred embodiment, the reaction mixture is passed through a hot tube packed with an inert material, for example, quartz chips or stainless steel helices. The product can be recovered by distillation. The product wherein the aromatic compound is benzene corresponds to the formula

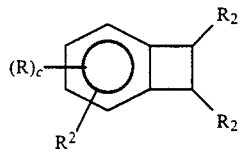

wherein R, $R^2$ and c are as hereinbefore defined.

In the preferred embodiment wherein $R^2$ is a hydrocarbyloxy carbonyl moiety, the hydrocarbyloxy carbonyl moiety can be converted to a carboxylate moiety by contacting the substituted (arylcyclobutene) compound with at least a molar equivalent of alkali metal hydroxide in an alkanol-water solvent system. In the embodiment wherein the aromatic radical is benzene, the product corresponds to the formula

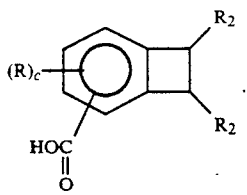

Thereafter the carboxylate-substituted (arylcyclobutene) compound can be converted to an acid chloride by contacting the carboxylate-substituted (arylcyclobutene) compound with thionyl chloride and refluxing at 70° C. to 80° C. The acid halide-substituted (arylcyclobutene) so formed can be used to prepare the novel monomers of this invention, as described hereinafter. In the embodiment wherein the aryl radical is a benzene ring, the product corresponds to the formula

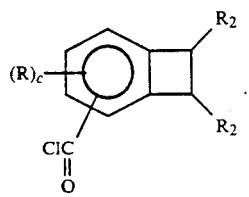

In an alternative synthesis, an aryl compound with ortho dibromomethyl groups can be converted to a 1,2-diiodoarylcyclobutene, by contacting the aryl compound substituted with ortho dibromomethyl moieties with an alkali metal iodide in an alkanol solvent at reflux so as to form the diiodoarylcyclobutenes. The product can be recovered by filtering, evaporating the filtrate and recrystallizing the product. In the embodiment wherein the aryl radical is a benzene radical, the starting material corresponds to the formula

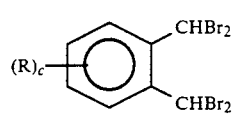

and the iodobenzocyclobutene corresponds to the formula

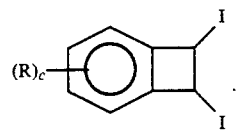

The 1,2-diiodoarylcyclobutenes can be converted to arylcyclobutenes by dissolving the 1,2-diiodoarylcyclobutenes in an alcohol solvent, preferably methanol or ethanol and contacting the solution with an alkali metal hydroxide in the presence of a palladium-on-carbon catalyst and $H_2$ gas at a temperature of 20° C. to 30° C. In general, at least between about 2 and 4 moles of alkali metal hydroxide per mole of 1,2-diiodoarylcyclobutene is used. Preferably, between about 50 and 200 psi of hydrogen gas is used. The arylcyclobutenes prepared in this manner can be recovered by distillation. In the embodiment wherein the aryl radical is a benzene radical, the product corresponds to the formula

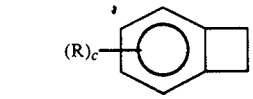

The arylcyclobutene can thereafter be brominated. In this process, the arylcyclobutene is dissolved in acetic acid and contacted with a brominating agent of pyridinium perbromide hydrobromide in the presence of mercuric salts, for example, mercuric acetate, at a temperature of between about 20° C. and 50° C. The brominated product can be recovered by extraction and distillation. In the embodiment wherein aryl radical is benzene, the product corresponds to the formula

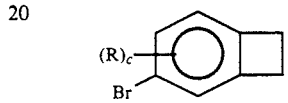

The brominated arylcyclobutene can thereafter be carbonylated to prepare a hydrocarbyloxy carbonyl-substituted arylcyclobutene. This carbonylation is achieved by dissolving the brominated arylcyclobutene in an alkanol solvent, and thereafter contacting the solution with carbon monoxide under pressure in the presence of a palladium catalyst, wherein the palladium is in the zero valence state, in the further presence of an acid acceptor under conditions such that the brominated arylcyclobutene compound undergoes carbonylation. Preferred catalysts are complexes prepared from palladium acetate and triphenyl phosphine, palladium triphenyl phosphine tetrakis, and bis(triphenyl phosphine) palladium chloride complex. The acid acceptor is generally a tertiary amine. In general, the reaction vessel is pressurized with carbon monoxide to a pressure of between atmospheric and 3000 psi, preferred pressures are between 600 and 1000 psi.

This process is preferably performed at a temperature of between 100° C. and 140° C., most preferably between 120° C. and 130° C. The hydrocarbyloxy carbonyl arylcyclobutene can be recovered by filtering off the catalyst, washing away the acid scavenger with a 10 percent strong mineral acid solution, stripping off the solvent and distilling. To prepare a carboxamide-substituted arylcyclobutene, a primary or secondary amine is substituted for the alcohol solvent. In the embodiment wherein the aryl radical is a benzene radical, the process corresponds to the following equation:

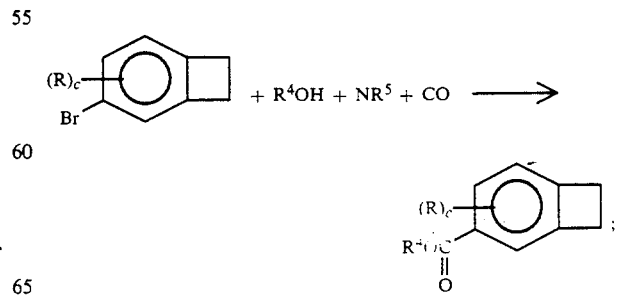

wherein R and c are as hereinbefore defined and $R^4$ and $R^5$ are hydrocarbyl moieties. The hydrocarbyloxy carbonyl-substituted or carboxamide-substituted arylcyclobutenes can thereafter be acidified and converted to acid chlorides by the process described hereinbefore.

The chlorocarbonyl-substituted arylcyclobutene compounds can be converted to poly(arylcyclobutene) compounds by contacting the halocarbonyl-substituted arylcyclobutenes with active hydrogen-containing compounds. Active hydrogen-containing compound refers herein to any compound which contains a hydrogen atom bonded to an oxygen, sulphur, phosphorus or nitrogen atom. For the purposes of this invention, an active hydrogen-containing compound refers to a compound containing a hydrogen atom which, because of its position in the molecule, displays significant activity according to the Zerewitnoff test described by Woller in the *J. Am. Chem. Soc.*, 49, 3181 (1927). Illustrative of such active hydrogen moieties are —COOH, —OH, —NH$_2$, =NH, —CONH$_2$, —SH, and —CONH—. Such active hydrogen-containing compounds include polyols, polyamines, polyimides, polymercaptans, polyacids and the like. To prepare a poly(arylcyclobutene) compound wherein the linking group is an amide, one contacts the halo carbonyl arylcyclobutene with a polyamine. To prepare a poly(arylcyclobutene) wherein the linking group is an imide, the active hydrogen-containing compound is a polyamide. To prepare a poly(arylcyclobutene) wherein the linking group is an ester, the active hydrogen-containing compound is an alcohol. To prepare a poly(arylcyclobutene) wherein the linking group is an anhydride, the active hydrogen-containing compound is an acid. The active hydrogen-containing compounds useful in this invention generally correspond to the formula

B—(H)$_n$ wherein B and n are as hereinbefore defined. More preferably the active hydrogen-containing compound corresponds to the following formula

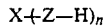

X—(Z—H)$_n$ wherein X, Z and n are as hereinbefore defined.

An alternative method to prepare a poly(arylcyclobutene) monomer with a polyamido(hydrocarbpoly-yl)-bridging member involves reacting a polyamino hydrocarbon with at least one equivalent of a hydrocarbyloxy carbonyl arylcyclobutene for each amino moiety on the hydrocarbon. The reactants are dissolved in an equal volume of 1,2,4-trichlorobenzene and heated to 170° C. for about 6 hours. The alkanol by-product generated can be removed by distillation or absorption on a molecular sieve. The solvent is removed by washing it away with ethyl ether. The product prepared results in an amide-linking group wherein the nitrogen atom is bound to the aryl radical.

In another preparation of an arylcyclobutene, the reaction may follow that reported by Skorcz and Kaminski, *Org. Syn.*, 48, pages 53–56 (1968). In a typical preparation, an alkyl cyanoacetate is added to a solution of sodium metal in ethanol followed by the addition of an ortho-halomethylaryl halide. The alkyl 3-(0-haloaryl)-2-cyanopropionate is isolated and treated with aqueous sodium hydroxide. Subsequent acidification results in the cyanoacetic acid derivative. That derivative is placed into N,N-dimethylformamide and is refluxed to form the 3-(0-haloaryl)propionitrile derivative which is isolated and added to a suspension of sodamide in liquid ammonia. After an appropriate reaction time, ammonium nitrate is added and the ammonia allowed to evaporate. The cyanoarylcyclobutene is isolated by ether extraction and purified by fractional distillation under reduced pressure.

Substituted arylcyclobutenes can be prepared by the same technique by using the appropriately substituted reactants, such as an alkyl or alkoxybenzyl halide. Also substituents can result from using an alkyl haloacetate, alkyl acetoacetate or a dialkylmalonate.

In another preparation based on the paper by Matsura et al., *Bull. Chem. Soc. Jap.*, 39, 1342 (1966), o-aminoaryl carboxylic acid is dissolved in ethanol and hydrochloric acid added. Isoamylnitrite is slowly added to the cold stirred solution and diethyl ether is then added. The product, aryldiazonium-2-carboxylate hydrochloride, is filtered. That product is placed in a solvent, preferably ethylene dichloride, and acrylonitrile and propylene oxide is added to the stirred mixture which is then heated under nitrogen until the reaction is complete. After cooling, the mixture is filtered and the product, 1-cyanoarylcyclobutene, is isolated by fractionally distilling the filtrate under reduced pressure.

Amounts of reactants, reaction parameters and other details can be found in the cited article, the examples of this application, or can be easily deduced therefrom.

In a next sequence of reactions, the cyanoarylcyclobutene or substituted derivative is nuclear substituted. When the poly(arylcyclobutene) to be prepared has an amide-linking group, the cyanoarylcyclobutene is aminated. In one preparation, the cyanoarylcyclobutene is added slowly to a cold solution of sodium nitrate in concentrated sulfuric acid to form 5-nitro-1-cyanoarylcyclobutene. That nitro compound is isolated, dissolved in ethanol and reduced by hydrogenation over a palladium on carbon catalyst. The isolated product is 5-amino-1-cyanoarylcyclobutene. In the preferred embodiment where the aryl radical is benzene, the product corresponds to the formula

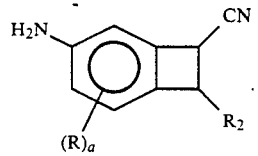

In another method of preparing the poly(arylcyclobutene) monomers, the amino-substituted arylcyclobutene is reacted with an appropriate coupling material. Coupling material refers herein to a compound which reacts with the amino or other substituent on the arylcyclobutene so as to form a bridging member with the amino or other substituent. Such processes are described hereinafter. In the embodiment wherein the bridging member contains amide-linking groups, the amino-substituted arylcyclobutenes are reacted with a polyvalent acid chloride. In practice, the amine-substituted arylcyclobutene is dissolved in a chlorinated aliphatic hydrocarbon solvent to which is added a tertiary amine, the acid acceptor, and thereafter the polyvalent acid chloride in a chlorinated aliphatic hydrocarbon solvent is added slowly to the mixture. This is preferably done at about 0° C. in an inert atmosphere. It is preferred to stir the reaction mixture for a period of time at 0° C. after the addition is complete.

To prepare a hydroxy-substituted arylcyclobutene, an amine-substituted arylcyclobutene is contacted with an alkali metal nitrite in the presence of sulfuric acid at 0° C., and thereafter the reaction mixture is heated to 100° C.

To prepare a mercapto-substituted arylcyclobutene, first an arylcyclobutene is reacted with chlorosulfonic acid to prepare an arylcyclobutene sulfonyl chloride. Arylcyclobutenyl sulfonyl chloride is reacted with zinc to prepare a mercapto-substituted arylcyclobutene. Alternatively, the arylcyclobutene is treated with a mixture of sulfur trioxide and dioxane at 0° C. followed by treatment with water. The arylcyclobutene-sulfonic acid is isolated and treated with phosphorous pentachloride to form the arylcyclobutene sulfonyl which is then reduced with zinc to the mercapto-substituted arylcyclobutene.

An iodo-substituted arylcyclobutene can be prepared by reacting an amino-substituted arylcyclobutene with an alkali metal nitrite, sulfuric acid and potassium iodide at 0° C. under conditions such that an iodoarylcyclobutene is prepared.

An alkenyl-substituted arylcyclobutene can be prepared by reacting a bromo-substituted arylcyclobutene with an alkene, wherein the alkene contains a terminal olefin, in an aliphatic hydrocarbon solvent in the presence of a palladium catalyst such as palladium acetate, and a tertiary amine such as triethylamine. It is advantageous to use a slight excess of the bromo-substituted arylcyclobutene. The tertiary amine, which functions as an acid acceptor, is used in equimolar amounts with the bromo-substituted arylcyclobutene. The palladium catalyst is used in catalytically effective amounts. Generally this process can be performed at temperatures of between about 40° C. and 140° C.

Cyclobutapyridines are prepared by the pyrolysis of 4-pyridyl propargyl ether at 550° C. See J. M. Riemann et al. *Tetrahedron Letters*, No. 22, pp. 1867–1870 (1977), incorporated herein by reference. Alternatively, a pyridine-4-carbonitrile with an alkyl substituent on the carbon atom adjacent to the nitrile is reacted with sodium azide and ammonium chloride in N,N-dimethylformamide to prepare a 5(alkyl-4-pyridyl)tetrazole. The 5(alkyl-4-pyridyl)tetrazole is pyrolyzed at about 600° C. to prepare a cyclobutapyridine. See W. D. Crow et al. *Australian Journal of Chemistry* 1741 et seq. (1975) incorporated herein by reference.

Amino cyclobutapyridines are prepared by reacting a cyclobuta pyridine with sodamide (NaNH$_2$) in N,N-dimethyl aniline solvent at 110° C. A hydroxycyclobutapyridine is prepared by reacting one mole of an aminocyclobutapyridine with one mole of sodium nitrite and two moles of sulfuric acid in water at 0° C. for a period of time and thereafter warming to 50° C. Halo-substituted cyclobutapyridine is prepared by reacting a hydroxypyridine in thionyl at reflux either neat or halide, for example, thionyl chloride or thionyl bromide, in N,N-dimethylformamide solvent.

To prepare a poly(arylcyclobutene) with an alkene-poly-yl or alkenar-poly-yl-bridging member, an alkene or alkene-substituted aromatic compound which contains two or more terminal olefinic moieties is reacted with at least one mole of a bromo-substituted arylcyclobutene for each terminal olefin under conditions described hereinbefore.

To prepare a poly(arylcyclobutene) monomer in which the bridging member contains an amine-linking group, the amine-substituted arylcyclobutene is reacted with a polyvalent alkyl halide. In order to prepare a poly(arylcyclobutene) monomer in which the bridging member contains a linking group which is ureylene, the amine-substituted arylcyclobutene is reacted with a polyvalent isocyanate or phosgene.

To prepare a poly(arylcyclobutene) monomer in which the bridging member contains a linking group of a cyclic imide, the amine-substituted arylcyclobutene is reacted with a polyvalent anhydride compound.

To prepare a poly(arylcyclobutene) monomer with a polyvalent organic bridging member containing carbonyl-linking groups, the arylcyclobutene is reacted with an acid chloride with two or more acid chloride moieties, in the presence of aluminum chloride, or antimony pentachloride.

To prepare a poly(arylcyclobutene) monomer with a polyvalent organic bridging member containing an ammonium carboxylate-linking group, a carboxylate-substituted arylcyclobutene is contacted with a polyvalent polyamine-substituted compound.

To prepare a poly(arylcyclobutene) with a polyvalent organic bridging member containing thio-linking groups, a mercapto-substituted arylcyclobutene is reacted with an alkali metal hydroxide to prepare an alkali metal salt of the mercapto-substituted arylcyclobutene. The salt is then reacted with a polyhalo organic compound to prepare a poly(arylcyclobutene) with an organic bridging member containing thio-linking groups.

To prepare a poly(arylcyclobutene) with a polyvalent organic bridging member containing nitrogen (amino)-linking groups, two or more equivalents of an amino-substituted arylcyclobutene are reacted with an organic compound containing two or more aldehyde moieties in the presence of an alkali metal cyanoborohydride under conditions that a poly(arylcyclobutene) with a polyvalent organic bridging member with amino-linking moieties is prepared. One equivalent of amino-substituted arylcyclobutene for each aldehyde moiety on the organic aldehyde-containing compound is used. Alternatively, two or more equivalents of amine-substituted arylcyclobutene are reacted with an organic compound containing two or more bromo moieties in the presence of an alkaline earth metal carbonate under conditions such that a poly(arylcyclobutene) with an organic bridging member containing amino-linking moieties is prepared. An equivalent of amino-substituted arylcyclobutene is used for each bromo moiety on the bromo-substituted organic compound.

To prepare poly(arylcyclobutene) monomers with polyvalent organic bridging members containing oxygen-linking moieties, a hydroxy-substituted arylcyclobutene is contacted with an alkali metal hydroxide to prepare an alkali metal salt of a hydroxy-substituted arylcyclobutene. Two or more equivalents of the salt is then reacted with an organic compound containing two or more bromo moieties, under conditions such that a poly(arylcyclobutene) with an organic bridging member containing oxygen-linking groups is prepared. One equivalent of the salt for each bromo moiety on the organic compound is used.

An alternative method of preparing the poly(arylcyclobutene) monomers wherein a carbonyl group is attached to the aryl moiety involves contacting the carboxylate-substituted arylcyclobutenes with 1',1-carbonyldiimidazole in an ether solvent at 0° C. The reaction mixture is then heated until it reaches the reflux of the solvent and thereafter any active hydrogen-containing compound is added so as to prepare a poly (arylcyclobutene) monomer, wherein the bridging member contains a carbonyl group which is bonded to the aryl group of the arylcyclobutene.

In order to prepare a polysiloxane bridging member, the amino-substituted arylcyclobutene is reacted with a polychlorinated polysiloxane. Alternatively, a halocarbonyl-substituted arylcyclobutene is reacted with an aminoalkylterminated polysiloxane.

To prepare a poly(arylcyclobutene) monomer with a polyvalent organic bridging member comprising a carbonyl moiety, an acid-halide-substituted (arylcyclobutene) is reacted with an arylcyclobutene in the presence of $AlCl_3$, $SnCl_4$, or $SbCl_5$.

To prepare a poly(arylcyclobutene) with a carbonyldioxy inorganic bridging member, two moles of a hydroxy-substituted arylcyclobutene is reacted with phosgene in the presence of a tertiary amine. To prepare a poly(arylcyclobutene) with a bridging member of a polyvalent metal ionically bonded to a polyvalent carboxylate moiety, a carboxylate-substituted arylcyclobutene is reacted with a metal hydroxide to prepare a metal poly(arylcyclobutene) carboxylate. In general, the metal hydroxide is reacted with the number of moles of carboxylate-substituted arylcyclobutenes equal to the metal's coordination number. A poly(arylcyclobutene) with a polyvalent metal bridging member is prepared by first reacting one equivalent of a bromine-substituted arylcyclobutene with one equivalent of magnesium in an ether solvent to prepare an arylcyclobutenyl magnesium bromide. To prepare a di(arylcyclobutenyl) magnesium, one equivalent of a brominated arylcyclobutene is reacted with two equivalents of magnesium. The arylcyclobutenyl magnesium bromide is reacted with a metal chloride to prepare a poly(arylcyclobutenyl) metal. The metal chloride is reacted with the number of equivalents of arylcyclobutenyl magnesium bromide equal to the metal's oxidation state.

To prepare a poly(arylcyclobutene) with an inorganic bridging member of sulfur, a mercapto-substituted benzocyclobutene is reacted with an iodo-substituted arylcyclobutene in an amide solvent in the presence of an alkali metal hydroxide. Alternatively, the mercapto-substituted arylcyclobutene can be reacted with cuprous chloride to prepare a cuprous salt of a mercapto-substituted arylcyclobutene. The salt can thereafter be reacted with an iodo-substituted cyclobutene butene in an amide solvent to prepare a poly(arylcyclobutene) with a sulfide bridging member. The sulfide bridging member can be converted to a sulfoxide by contacting the poly(arylcyclobutene) sulfide with one equivalent of peracetic acid under conditions to oxidize the sulfide to a sulfoxide. Alternatively, the sulfide can be converted to a sulfone by contacting the poly(arylcyclobutene) with two equivalents of peracetic acid under conditions to oxidize the sulfide to a sulfone.

To prepare a poly(arylcyclobutene) with a phosphorus bridging member, an arylcyclobutene magnesium bromide is reacted with phosphorus trichloride to prepare a tri(arylcyclobutenyl) phosphine. The tri(arylcyclobutenyl) phosphine can be contacted with peracetic acid, so as to prepare a tri(arylcyclobutenyl) phosphine oxide.

To prepare a poly(arylcyclobutene) with a nitrogen bridging member, an amino-substituted arylcyclobutene is reacted with a potassium hydride to prepare a potassium salt of an amine-substituted arylcyclobutene. The salt is then reacted with an iodoarylcyclobutene in liquid ammonia under ultraviolet light, under conditions that a poly(arylcyclobutene) with a nitrogen bridging member is prepared.

To prepare a poly(arylcyclobutene) with an oxygen bridging member, two equivalents of a hydroxy-substituted arylcyclobutene are reacted with cupric carbonate to prepare cupric salt comprising a copper cation and two anions of hydroxyarylcyclobutenes from which the hydroxyl hydrogens have been abstracted. The salt is then reacted with an iodoarylcyclobutene, at between 100° C. and 180° C., either neat or in an amide solvent, under conditions such that a di(arylcyclobutene) ether is prepared.

To prepare the various bridged poly(arylcyclobutenes) wherein the aryl moiety is a heterocycle, the appropriately substituted heterocyclic arylcyclobutene is reacted in the manner described herein to get the appropriately desired compound. For example, one mole of hydroxy substituted cyclobutapyridine is reacted with a polyacid halide in the presence of triethylamine in a chlorinated solvent at 0° C., with warming to 20° C. to prepare a poly(arylcyclobutene) with carbonyldioxy linking moieties. To prepare a poly(arylcyclobutene) wherein the aryl moiety is pyridine, with amide linking groups in the bridging member, an amino-substituted cyclobutapyridine is reacted with a polyacid chloride in the presence of triethylamine in a dichloromethane solvent at 0° C., then at 20° C. Generally, one mole of amino-substituted cyclobutapyridine and triethylamine is used for every equivalent of acid chloride. A poly(arylcyclobutene) wherein the aryl moiety is pyridine with sulfur linking groups is prepared by the following procedure. A chloro-substituted cyclobutapyridine is reacted with a polythiol in the presence of sodium ethoxide in an ethanol solvent at reflux. One mole of chloro-substituted cyclobutapyridine and sodium ethoxide is used for each equivalent of thiol.

In that embodiment wherein the bridging group is alternating alkenyl and aryl moieties for example

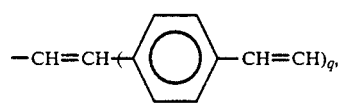

a compound of the formula one mole

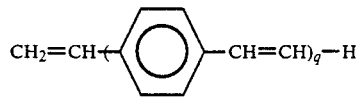

is reacted with two moles of a bromo-substituted cyclobutapyridine in the presence of palladium (II) acetate (0.02 moles) and tri-o-tolylphosphene (0.06 moles) in acetonitrile solvent, at reflux for four hours.

The novel poly(arylcyclobutene) compounds of this invention are useful in the preparation of polymeric compositions. In general, these polymeric compositions are prepared by contacting one or more of the poly(arylcyclobutene) compounds and heating them to the polymerization temperature of the particular monomer(s) used. The polymerization is an addition polymerization wherein no volatiles are generated. Furthermore, no catalyst initiator or curing agents are necessary for the polymerization to take place. It is believed that the polymerization takes place when the cyclobutene ring undergoes transformation to prepare a molecule containing a 1,3-cyclohexadienyl radical with two exo-olefinic unsaturated moieties adjacent to one another wherein each of the olefinic unsaturated moieties undergoes reaction with the olefinic unsaturated moieties of other 1,3-cyclohexadienyl-containing molecules which have undergone the same transformation. The temperature at which the poly(arylcyclobutene) monomers undergo polymerization is affected by the nature of any substituent on the cyclobutene ring. In some embodiments, the temperature of polymerization is as low as about 30° C. In preferred embodiments, the temperature at which polymerization is initiated is above 150° C., more preferably above about 200° C. It is to be noted that the temperature at which polymerization is initiated is dependent upon the nature of substituents on the cyclobutene ring. In general, wherein the cyclobutene ring is unsubstituted, the polymerization is initiated at about 200° C. Wherein the cyclobutene ring is substituted with an electron-donating substituent, the polymerization temperature is generally lowered, the higher the ability of the substituent to donate electrons, the lower the polymerization initiation temperature is. Conversely, the electron-withdrawing substituents on the cyclobutene ring result in higher polymerization initiation temperatures. The unsubstituted cyclobutene in general polymerizes at the highest temperature.

It is believed the polymers prepared from the poly(arylcyclobutenes) comprise units corresponding to the formulas

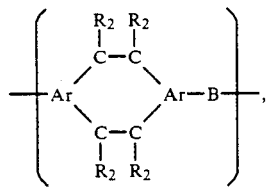

A

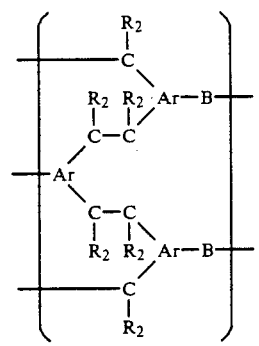

B or mixture thereof. It is believed that the preferred polymers prepared from the poly(arylcyclobutenes) comprise mixtures of formulas A and B.

In those embodiments wherein Ar is benzene, it is believed that the polymer's prepared from poly(benzocyclobutenes) comprise units corresponding to the formulas

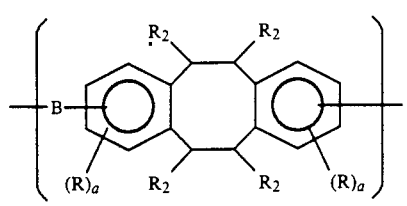

C or

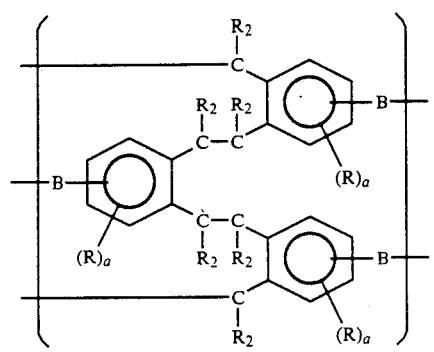

D or mixtures thereof. It is believed the preferred polymers prepared comprise mixtures of formulas C. and D with D being predominant.

The method of polymerization of the poly(arylcyclobutene) monomers has a significant effect on the nature and properties of the polymeric composition prepared. In one embodiment, the poly(arylcyclobutene) monomers of this invention can be melt polymerized. The melt polymerization of poly(arylcyclobutene) monomers allows their use in the preparation of solid parts, as coatings, in composites, as adhesives and as fibers.

In one embodiment of the melt polymerization, the monomer is melted at a temperature of between about 80° C. and 200° C., and thereafter poured or injected into a mold. Thereafter, pressure is applied on the melted monomer in the mold. Generally, pressures of between about 100 and 2000 psi are suitable. Thereafter, the monomer is heated to a temperature of between about 200° C. and 300° C., preferably between about 200° C. and 250° C. for between about 10 minutes and 3 hours. Upon cooling, the polymerized composition can be removed from the mold.

Polymers prepared in this manner can subsequently be thermally treated at temperatures above 200° C. to raise the modulus and lower the coefficient of expansion of such polymeric compositions.

In general, the polymers prepared by this method are insoluble in that they swell but do not dissolve, are thermally stable at 200° C., have a good modulus, a low water pickup and are reasonably hard.

Suitable fillers and reinforcing materials are, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered carborundum, chalk, iron powder, aluminum powder, sand, gravel and other fillers of this kind, also inorganic or organic fibers, more especially glass fibers in the usual textile forms of fibers, filaments rovings, yarns, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The end products combined with fillers or reinforcing materials may be used in particular in vessel and pipe construction by the winding technique, in electrical engineering, in mold construction and tool making and also in the construction of heavily stressed components, in the lightweight construction of vehicles in aeronautical and astronautical engineering.

In another embodiment, the poly(arylcyclobutene) monomers of this invention can be used to prepare coatings and films. In one embodiment, the monomers are dissolved in a suitable solvent and coated onto the substrate of choice, and thereafter the coated substrate is exposed to temperatures of above the polymerization temperature of the monomer. Preferably, the polymerization temperature is 150° C. or above, more preferably 200° C. or above. The coated substance is exposed to polymerization temperatures for a sufficient time for the polymerization to be completed. Preferably, such exposure times are between 1 and 5 hours. Suitable solvents are those which volatilize away at temperatures below the polymerization temperature. Preferred solvents are cyclic and aliphatic ethers, lower alkanols, amides, and chlorinated hydrocarbon solvents. It is preferable to saturate the solvent with the monomer, a 20 to 30 weight percent concentration of monomer in the solvent is more preferred.

The poly(arylcyclobutene) monomers may be combined with the powder-form or fibrous fillers or reinforcing materials either before or after heat treatment. For example, it is possible to impregnate powder-form or fibrous fillers or reinforcing materials such as quartz sand or glass cloths, with the poly(arylcyclobutene) monomers, optionally in solution.

In another embodiment, a film can be prepared from the poly(arylcyclobutene) monomers of this invention by powder coating techniques. In particular, the monomer in a powder form is placed on a desired substrate. Thereafter, the monomer is heated to its melt temperature over a time sufficient to melt the monomer and allow the melted monomer to form a liquid coating on the substrate. Thereafter, the melted monomer coated on the substrate is exposed to temperatures at which the monomer polymerizes for a time sufficient for the monomer to form a film on the desired substrate In another embodiment, the poly(arylcyclobutene) monomers can be used as adhesives. In such embodiment, one of the substrates to be joined is contacted with some form of the monomers, for example, the monomer in a powdered form. Thereafter, the second substrate to be adhesivated is contacted with the substrate previously contacted with the monomer. Thereafter, pressure of at least 1 psi is applied and the monomers and substrates are raised to a temperature at which the monomer undergoes polymerization.

In one embodiment, the poly(arylcyclobutene) monomers can be formed into a prepolymer which thereafter can be polymerized To form the prepolymer, the poly(arylcyclobutene) monomers are contacted in an inert atmosphere or under vacuum and heated to a stage at which the polymerization mixture is sufficiently viscous enough to be moldable in conventional molding equipment. Preferably, the monomers can be contacted at a temperature of 190° C. to 220° C. for between about 1 and 10 minutes. Thereafter, the prepolymer can be used in various techniques to prepare the polymeric compositions of this invention. In one preferred embodiment, the prepolymer is cooled to form a powder which can be used to form compression molded articles, as an adhesive, and in many other uses.

In another embodiment, a prepolymer of the poly(arylcyclobutene) monomers can be prepared by precipitation polymerization. In particular, the technique involves heating such monomers in a solvent to prepare a low molecular weight prepolymer. A solvent is used which dissolves the monomer but not the prepolymer. As the prepolymer forms, it precipitates and is removed. The prepolymer can be fabricated in a hot compression mold which reacts out the remaining arylcyclobutene rings to give a thermoset polymer. The product is a fine white powder. Preferable solvents are nonpolar solvents, such as aromatic hydrocarbons, aliphatic hydrocarbons, aliphatic chlorinated hydrocarbons, aromatic chlorinated hydrocarbon solvents, biphenols, naphthalenes or polychlorinated biphenyls. In general, the monomer can be dissolved up to saturation in the solvent used. A 20 to 30 percent by weight solution of the monomer in the solvent is preferred. The prepolymer is used to prepare a polymer by heating the prepolymer in the desired form, to the polymerization temperature of the monomer for a time sufficient for the polymerization to go to completion.

The polymerization preferably takes place at temperatures of between about 200° C. and 240° C. for periods of between about 1 and 5 hours.

In another embodiment, the poly(arylcyclobutene) monomers can be polymerized by solution polymerization techniques. In this embodiment, the monomers are dissolved in dipolar aprotic solvents with boiling points above the polymerization temperature of the monomers. It is preferable that the solvents have a boiling point of near or above 200° C. and more preferable that the solvents have a boiling point of above 250° C. Examples of preferred dipolar aprotic solvents include amides and sulfones. It is necessary to add to the solution lithium salts which solubilize the polymer in the solvents, preferably, between about 5 and 20 weight percent based on the solvent weight. A preferred lithium salt is lithium chloride. The polymerization takes place by heating the polymerization solution to a temperature at which the monomer undergoes polymerization, preferably above 200° C. The polymerization time is preferably between about 1 and 10 hours. The polymer can be recovered by adding water to precipitate the polymer from the reaction solution and thereafter stripping off the solvent. The polymers prepared with this method can be used in compression moldings or to prepare coatings.

In another embodiment, the monomers of this invention which undergo polymerization at a temperature which is below the melting point of the monomer can be polymerized in a solid state polymerization. In this method, the monomer is heated to a temperature at which polymerization takes place. Polymers prepared in this method can be useful in the preparation of bearings, seals and other parts by powder metallurgy techniques.

SPECIFIC EMBODIMENTS

The following examples are included for illustrative purposes only, and do not limit the scope of the invention or the claims. Unless otherwise specified, all parts and percentages are by weight

EXAMPLE 1

Chloromethylation of Methyl Para-toluate

A solution of methyl para-toluate (30 g, 0.20 mole) in 1,2-dichloroethane (80 ml) is added to a flask equipped with ice bath, stirrer, water-cooled condenser, ice traps and scrubber. To the stirred solution is added chloromethyl methyl ether (48 ml, 0.63 mole), thionyl chloride (5.8 ml, 0.080 mole), and last ferric chloride (6.5 g, 0.040 mole) in two portions. The cooling bath is removed, and the stirred reaction mixture is heated at 60° C. (heating lamp, controller) for 3 hours.

Methanol (150 ml) is added gradually to the cooled reaction mixture (exotherm). Low boiling components are removed under vacuum. The solution of product in dichloroethane is washed with water, 5 percent sodium bicarbonate solution, dried over anhydrous magnesium sulfate, filtered, and solvent is removed under vacuum. The product contains 13 percent unreacted methyl para-toluate and 80 percent methyl 3-chloromethyl-4-methylbenzoate (CMMT-chloromethylated methyl toluate) as analyzed by capillary gas chromatography. Recovery of the starting material by vacuum distillation affords a distillation residue of 91 percent pure product (analysis by capillary gas chromatography).

EXAMPLE 2

Pyrolysis of Methyl(3-Chloromethyl)Para-toluate to Prepare 4-Carbomethoxybenzocyclobutene The experimental setup is a quartz tube packed with quartz chips. The central portion of the tube is placed in a furnace. A 25-centimeter portion of the tube above the furnace serves as a preheating zone and the temperature in the middle of such preheating zone is between about 250° C. and 300° C. Attached to the top of the tube is an addition funnel. Attached to the bottom portion of the tube are cold traps and a means for pulling a vacuum on the tube. Methyl(3-chloromethyl)para-toluate (50 g) is dissolved in 200 g of ortho-xylene and placed in the addition funnel. The furnace is heated up to 730° C. A vacuum pump is turned on and pressure is adjusted to 25 mm of mercury. The solution of methyl(3-chloromethyl)para-toluate is added dropwise over a period of 1 hour and 15 minutes. Product and unreacted starting material are collected in cold traps. The pyrolytic tube is flushed with 200 ml of acetone after a cooling down period. The acetone solution is combined with the ortho-xylene solution collected in the cold traps. Acetone and ortho-xylene are distilled off with a 16-inch Vigreaux column under normal pressure. When most of the ortho-xylene is distilled, the system is brought to 0.02 mm mercury and 15.5 g of pure 4-carbomethoxybenzocyclobutene is collected at 61° C. The residue left in the distillation pot is methyl(3-chloromethyl)para-toluate, 23 g.

EXAMPLE 3

Preparation of 1-Cyanobenzocyclobutene

A mixture of benzenediazonium-2-carboxylate hydrochloride (1.92 g), acrylonitrile (0.80 g) and propylene oxide (0.58 g) in 100 ml of ethylene dichloride is stirred in a flask under nitrogen at 50° C.–60° C. for 4 hours. The mixture is cooled to room temperature and filtered. The filtrate is examined by gas chromatography and is found to contain 0.52 g (40 percent yield) of 1-cyanobenzocyclobutene.

EXAMPLE 4

Preparation of 5-Amino-1-Cyanobenzocyclobutene

The 1-cyanobenzocyclobutene is added slowly to a cold solution of sodium nitrate in cold sulfuric acid. The so-formed nitro compound is isolated, dissolved in ethanol, and reduced by hydrogenation over a palladium on carbon catalyst.

EXAMPLE 5

Preparation of 1,2-Diiodobenzocyclobutene

In a 12-liter, three-neck flask equipped with two reflux condensers and an air-driven stirrer, is placed 6.5 liters of absolute ethanol. The system is connected to a nitrogen line and bubbler through a three-way valve. The system is purged with nitrogen and 437.5 g (1.037 moles) of $\alpha, \alpha, \alpha', \alpha'$-tetrabromo-o-xylene and 1,948.1 g (12.98 moles) of sodium iodide are added with stirring. The reaction mixture is stirred and heated under reflux for 10 days under nitrogen. The mixture is cooled and the ethanol solvent removed with a rotary evaporator. The residue is stirred with methylene chloride and filtered. The filtrate is extracted with water and then stirred for 15 minutes with a 20 percent sodium sulfite solution. The methylene chloride layer is separated and extracted 4 times with water. It is then dried over magnesium sulfate and filtered. The methylene chloride is then removed on a rotary evaporator and the residue is treated with hot methanol. The insoluble tarry impurities are separated by decantation and the methanol solution is treated with activated charcoal. The methanol-charcoal mixture is boiled for 15 minutes and then filtered through celite to remove the charcoal. The charcoal treatment procedure is then repeated 4 more times. Following this, the methanol filtrate is placed in a round-bottom flask and the methanol is removed on a rotary evaporator to give the crude product as a beige solid. This is recrystallized from methanol to give 166.9 g of pure product. The filtrate from the recrystallization is evaporated to give an orange oil which, on treatment with methanol, yielded another 62.9 g of pure product. Total yield is 233.8 g or 63.3 percent.

EXAMPLE 6

Bromination Of Benzocyclobutene

The brominating agent used in this case is pyridinium hydrobromide perbromide ($C_5H_5N \oplus HBR_3 \ominus$, formula weight 319.86). This reagent is prepared just prior to its use via the method of Fieser, *Reagents for Organic Synthesis*, Fieser & Fieser, pp. 967–982.

A 2000-ml round-bottom, three-neck flask is equipped with a reflux condenser connected to a nitrogen line with T and mineral oil bubbler, mechanical stirrer, and a thermocouple attached to a temperature controller. The flask is then charged with 4.5 g of mercuric acetate ($Hg(O_2CCH_3)_2$, f.w. 318.68, 14.12 mmoles), 28.5 g of benzocyclobutene ($C_8H_8$, m.w.=104.15, 0.274 mole), and 950 ml of glacial acetic acid. This mixture is stirred, 60 g of pyridinium hydrobromide perbromide is added, and the reaction is heated to 50° C. After 4 hours, another 60 g of brominating agent is added. The mixture is sampled and the conversion of starting material to product is monitored by gas chromatography. The addition of 60-g increments of brominating agent proceeds in this manner until conversion is complete (4 days, 460 g of pyridinium hydrobromide perbromide total).

The reaction product is isolated by first decanting the acetic acid solution into a separatory funnel and diluting with 500 ml of water. The crystals of pyridinium hydrobromide perbromide are then soaked in methylene chloride (250 ml) to leach out any residual product. This methylene chloride solution is decanted into the separatory funnel, the funnel shaken, and the layers separated. The aqueous solution is returned to the funnel and the process is repeated twice more. The methylene chloride extracts are combined and washed with 500 ml of $Na_2SO_3$ (5 percent), 500 ml of water, 500 ml of aqueous hydrochloric acid (10 percent), 500 ml of water, 500 ml of $NaHCO_3$ (saturated), 500 ml of water, and dried over $MgSO_4$. The methylene chloride is then carefully removed via distillation, and the product is isolated by vacuum distillation using a column packed with stainless steel mesh. Bromobenzocyclobutene is collected at 58° C.-60° C. with a vacuum of 1.5 mm Hg. Total of 32 8 g is isolated pure, and the pot residue contains another 8-10 g of material. Isolated yield is 65.6 percent of theoretical value.

EXAMPLE 7

Carbonylation of 4-Bromobenzocyclobutene to Prepare 4-Carbomethoxybenzocyclobutene This reaction is run in a 450-ml Parr pressure reactor fitted with a magnetically coupled stirring system. Into this reactor is entered 30 g of 4-bromobenzocyclobutene (0.164 mole), 16.5 g of $(CH_3CH_2)_3N$ (0.164 mole, freshly distilled over Na metal), 100 ml of $CH_3OH$ (Burdick & Jackson brand), and the catalyst mixture of 1.1 g of $Pd(O_2CCH_3)_2$ (4.9 mmoles, 3 mole percent) and 1.1 g of $PPh_3$ (recrystallized from ethanol). The reactor is then sealed and attached to a CO cylinder. The mixture is purged with 600 psig CO three times while stirring, and finally pressurized and held at 600 psig CO. The temperature is raised to 125° C., and held under these conditions overnight (approximately 16 hours). After this time, the unreacted CO is vented, and the reaction vessel is cooled to ambient temperature. The methanol solution is diluted with 200 ml of water, and the product extracted with 3×150 ml of $CH_2Cl_2$. The methylene chloride solution is then washed with 250 ml of water, 250 ml of HCl (5 percent), 250 ml of water, 250 ml of $NaHCO_3$ (saturated), 250 ml of water, and dried over $MgSO_4$. The methylene chloride solution is checked for conversion by gas chromatographic analysis, and the composition is discovered to be 97 percent 4-carbomethoxybenzocyclobutene. The solvent is then removed by distillation, and the product is then purified by vacuum distillation at 66° C.-67° C., 1 mm Hg vacuum.

EXAMPLE 8

Preparation of Benzocyclobutene 4-Carboxylic Acid by Hydrolysis of 4-carbomethoxybenzocyclobutene A 500-ml round-bottom, single-neck flask is equipped with magnetic stirrer and reflux condenser attached to a nitrogen line with T mineral oil bubbler. To this flask is added 10 g of 4-carbomethoxybenzocyclobutene (m.w. 162.19 g, 0.062 mole) and 190 ml of methyl alcohol (Burdick & Jackson brand). This solution is stirred, and to it is added 60 ml of aqueous NaOH solution containing 7.5 g of NaOH (m.w. 39.998, 0.188 moles). This mixture is stirred at room temperature for one hour, after which the solution is transferred into a 1000-ml separatory funnel. The strongly alkaline solution is first diluted with 250 ml of water, and washed with 250 ml of $CH_2Cl_2$. The aqueous solution is then drained into a large beaker and acidified with concentrated HCl until the solution is strongly acidic. The acid, which forms a white precipitate upon acidification, is then collected with 3×250 ml of $CH_2Cl_2$. L- The methylene chloride solution is dried over $MgSO_4$ and the solvent removed via rotary evaporation. The carboxylic acid (8.95 g) is recovered as a white solid (98 percent of theoretical yield).

EXAMPLE 9

Preparation of Benzocyclobutene Acid Chloride and Reaction Thereof With A Diamine 4-Carbomethoxybenzocyclobutene (29.2 g) is hydrolyzed to benzocyclobutene-4 carboxylic acid using the procedure given under Example 8. The acid is dried and added to 50 ml of freshly distilled thionyl chloride in a 500-ml single-neck flask equipped with a reflux condenser, nitrogen blanket and magnetic stirrer. The mixture is refluxed under nitrogen for ½ hour. The excess thionyl chloride is removed with a vacuum pump leaving the so produced acid chloride as a brown oil. The product weighs 28.6 g and is used without further purification. The acid chloride is dissolved in 100 ml of methylene chloride and added to a 2-liter three-neck flask equipped with a thermometer port (the 2-liter flask and accessories are dried with a heat gun prior to adding the acid chloride). The flask is then equipped with a reflux condenser topped with a nitrogen line and mineral oil bubbler, an addition funnel fitted with a septum and a thermocouple probe placed in the thermometer port. Triethylamine (20 g) is then added to the flask Heptamethylene diamine (10.6 g) is weighed out into a bottle in a dry box and the bottle capped with a septum. The diamine is diluted with 100 ml of methylene chloride and transferred via a syringe to the addition funnel The diamine solution is then added dropwise to the reaction mixture. After this addition, the addition funnel is filled with methylene chloride and this is also added to the reaction mixture. This rinsing procedure is then repeated a second time. Finally, the reaction mixture is heated at reflux for 16 hours. The mixture is cooled to room temperature and poured into a separatory funnel The mixture is then washed successively with 500 ml of water, 500 ml of 5 percent hydrochloric acid, 500 ml of water, 500 ml of saturated sodium bicarbonate and finally dried over anhydrous magnesium sulfate. The methylene chloride is evaporated off to give the product as a light brown solid This is diluted with 250 ml of toluene and heated. The solution is then filtered (after cooling for 15 minutes) and the solid removed through this filtration is again dissolved in 250 ml of toluene. This solution is also heated, cooled for 15 minutes and filtered (suction). The solid removed by this filtration shows no coloration upon dilution with toluene so the solid is removed by suction filtration and dried in vacuo. The final weight of the product is 24.58 g resulting in a 77.2 percent yield based on the amount of diamine added.

EXAMPLE 10

Preparation of Diamide Monomers

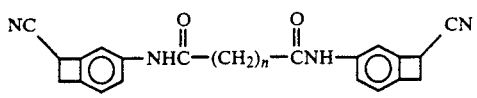

wherein n is the number of carbons between the carboxyl groups.

(a) n=2

5-Amino-1-cyanobenzocyclobutene (hereinafter called Compound A) (12.58 g, 0.089 mole) and triethylamine (7.05 g, 0.07 mole) are dissolved in 300 ml of methylene chloride. The solution is cooled to 0° C in an ice bath, with stirring unger argon. A solution of 6.91 g (0.045 mole) of succinyl chloride in 100 ml of methylene chloride is added dropwise to the cooled solution. The reaction mixture is stirred for 30 minutes at 0° C after the addition is complete. The reaction mixture is then warmed to room temperature and is poured into 400 ml of water. The mixture is extracted 3 times with 250-ml portions of methylene chloride. The combined methylene chloride extracts are washed once with 400 ml of a 5 percent hydrochloric acid solution. The methylene chloride layer is washed with 400 ml of water. Next, the methylene chloride solution is washed with 400 ml of saturated sodium bicarbonate and finally with 400 ml of water. The methylene chloride is removed under vacuum to give the product as a gray solid. Yield is 10 g or 60.6 percent.

(b) n=3

This monomer is prepared as under (a) using different amounts of reactants and is run in a nitrogen atmosphere. Compound A (12.13 g, 0.086 mole) and triethylamine (8.7 g, 0.086 mole) are dissolved in 300 ml of methylene chloride. Glutaryl chloride (6.61 g, 0.038 mole) is dissolved in 100 ml of methylene chloride and is added dropwise to the reaction mixture The reaction is run and worked up the same as under (a) except that the methylene chloride solution is dried over anhydrous magnesium sulfate, filtered and then concentrated under vacuum. The product is a green solid. The yield is 13 g, 86.6 percent.

(c) n=4

This monomer is prepared in the same manner as described in (a) using different amounts of reactants and is run in a nitrogen atmosphere. Compound A (11.7 g, 0.083 mole) and triethylamine (8.4 g, 0.083 mole) are dissolved in 300 ml of methylene chloride. Adipoyl chloride (6.90 g, 0.038 mole) is dissolved in 100 ml of methylene chloride and is added dropwise to the mixture. The workup of the reaction mixture is the same as under (b), obtaining 14.7 g (98 percent) of a white solid.

The product is recrystallized from ethanol to give 8 g (53.3 percent yield) of solid.

(d) n=5

Thionyl chloride (5.12 g, 0.043 mole) is added dropwise under nitrogen to 20 ml of dry N,N-dimethylformamide which is cooled and stirred for 30 minutes at 0° C. in an ice bath. Pimelic acid (3.20 g, 0.020 mole) is dissolved in 15 ml of dry N,N-dimethylformamide and is added dropwise to the cooled reaction mixture. The reaction mixture is stirred an additional 30 minutes and then is warmed to room temperature and is stirred another 30 minutes, then again is cooled to 0° C in an ice bath. Compound A (6.77 g, 0.047 mole) and triethylamine (6.06 g, 0.060 mole) are dissolved in 20 ml of dry N,N-dimethylformamide. This solution is then added dropwise to the cooled reaction mixture. The reaction mixture is slowly warmed to room temperature overnight The reaction mixture is poured into 500 ml of water and is stirred for 30 minutes. Next, the water layer is extracted then washed twice with 200-ml portions of chloroform. The chloroform washes are combined and washed once with 300 ml of a saturated sodium bicarbonate solution, and once with 300 ml of water. The chloroform solution is washed once with 300 ml of a 10 percent hydrochloric acid solution and finally with 300 ml of water. The chloroform solution is then dried over anhydrous magnesium sulfate, filtered and concentrated under vacuum The product obtained is column chromatographed over silica gel using ethyl acetate as the eluting solvent. A yellow colored solid is obtained.

(e) n=6

This monomer is prepared by the same procedure that is used under (d) except that 0.02 mole suberic acid was employed, and 0.048 mole of Compound A and 0.061 mole of triethylamine are dissolved in 15 ml of N,N-dimethylformamide and are added to the cooled reaction mixture. A white solid is obtained.

(f) n=7

This monomer is prepared by the method used under (d). Thionyl chloride (4.53 g, 0.038 mole) is added while stirring to 20 ml of dry N,N-dimethylformamide. Azelaic acid (3.33 g, 0.018 mole) is dissolved in 15 ml of N,N-dimethylformamide and is added to the reaction mixture at 0° C. The reaction mixture is then stirred as indicated previously under (d). Compound A (6.0 g, 0.042 mole) and triethylamine (5.37 g, 0.053 mole) are dissolved in 15 ml of N,N-dimethylformamide and added dropwise to the cooled reaction which is worked up as in (d), obtaining a brown solid.

(g) n=8

This preparation involves dissolving Compound A (1.41 g, 0.01 mole) and pyridine (1.0 g, 0.013 mole) in 35 ml of methylene chloride. This solution is cooled to 0° C in an ice bath with stirring under nitrogen. Sebacoyl chloride (1.20 g, 0.005 mole) is dissolved in 15 ml of methylene chloride and is added dropwise to the cooled solution. The reaction mixture is stirred for 30 minutes at 0° C and is warmed to room temperature. The reaction mixture is poured into 100 ml of water and is extracted 3 times with 50-ml portions of methylene chloride. The methylene chloride extracts are combined and washed once with 100 ml of a 5 percent hydrochloric acid solution. The methylene chloride solution is then washed with 100 ml of water and is dried over anhydrous magnesium sulfate. The solution is filtered and concentrated under vacuum to obtain a white-colored solid. The solid product is dried under a vacuum overnight.

EXAMPLE 11

Preparation of Bisbenzocyclobutene With A Diamido Bridging Member

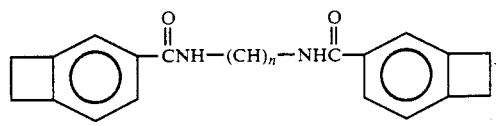

The general reaction sequence is to react benzocyclobutene 4-carboxylic acid with 1,1-carbonyl diimidazole to give an imidazole derivative which is further reacted with a polyalkyene diamine to result in the bis-amide monomer.

(a) n=3

1,1-Carbonyldiimidazole (2.64 g, 0.016 mole) is dissolved in 45 ml of dry tetrahydrofuran and stirred under nitrogen at room temperature. The benzocyclobutene 4-carboxylic acid (2.37 g, 0.016 mole) is dissolved in 45 ml of dry tetrahydrofuran and added dropwise to the stirred imidazole solution at room temperature. The mixture is stirred for 30 minutes at room temperature and then heated at reflux overnight. The mixture is then cooled to room temperature and a solution of 1,3-propanediamine (0.53 g, 0.0072 mole) in 25 ml of dry tetrahydrofuran added dropwise. After this addition, the mixture is stirred at room temperature for 1½ hours and then heated to reflux overnight. The mixture is cooled to room temperature and poured into 300 ml of water with stirring. The mixture is extracted with three 200-ml portions of methylene chloride. The methylene chloride extracts are combined and washed with three 400-ml portions of a 10 percent hydrochloric acid solution. Next, the methylene chloride extract is washed with one 500-ml portion of water followed by two washings with 400-ml portions of saturated sodium bicarbonate. Finally, the methylene chloride extract is washed with two 500-ml portions of water and dried over anhydrous magnesium sulfate. The magnesium sulfate is filtered off and the filtrate evaporated to yield 2.5 g of crude product. This is recrystallized from ethanol to yield 1.5 g (0.0045 mole) of pure product. The melting point of the product is 172° C.-178° C.

(b) n=5

The same procedure and workup is used as in the preceding example. The quantities of reactants and product are: benzocyclobutene 4-carboxylic acid (2.22 g, 0.015 mole); 1,1-carbonyldiimidazole (2.38 g, 0.0147 mole); 1,5-pentanediamine (0.72 g, 0.0071 mole); and product weight (1.8 g, 0.0049 mole). The melting point is 181° C.-185° C.

(c) n=6

The same procedure and workup is used as in the procedure where n=3. The quantities of reactants and product are: benzocyclobutene 4-carboxylic acid (2.22 g, 0.015 mole); 1,1-carbonyldiimidazole (2.43 g, 0.015 mole); 1,6-hexanediamine (0.79 g, 0.0068 mole); and product weight (0.65 g, 0.0017 mole). The melting point is 185° C.-194° C.

(d) n=7

The same procedure and workup is used as in the procedure where n =3. The quantities of reactants and product are: benzocyclobutene 4-carboxylic acid (2.22 g, 0.015 mole); 1,1-carbonyldiimidazole (2.48 g, 0.015 mole); 1,7-heptanediamine (0.99 g, 0 0076 mole); and product weight (0.6 g, 0.0015 mole). The melting point is 141° C.-145° C.

(e) n=8

The same procedure and workup is used as for the procedure where n =3. The quantities of reactants and product are: benzocyclobutene 4-carboxylic acid (1.48 g, 0.01 mole); 1,1-carbonyldiimidazole (1.62 g, 0.01 mole); 1,8-octanediamine (0.65 g, 0.0045 mole); and product weight (0.5 g, 0.0012 mole). The melting point is 172° C.-176° C.

EXAMPLE 12

Formation Of

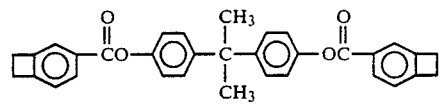

A 2000-ml three-neck, round-bottom flask is equipped with magnetic stirrer, 125-ml addition funnel, reflux condenser with nitrogen blanket, and stopper. To this system is added 25.62 g of 4,4'-isopropylidene diphenol (bisphenol A, m.w. 228.3 g, 0.1122 mole), 24.0 g of $(CH_3CH_2)_3N$ (0.238 mole, m.w. 101 freshly distilled over Na metal), and 600 ml of $CH_2Cl_2$. This flask is now cooled with an ice water bath to 10° C., with stirring, and 38.78 g of benzocyclobutene 4-acid chloride (m.w. 166.5 g, 0.233 mole) in 75 ml of $CH_2Cl_2$ is entered into the addition funnel. This solution is added dropwise to the stirring bisphenol A solution. When all of the acid chloride solution has been added, the addition funnel is washed with 2×100 ml of $CH_2Cl_2$. The reaction mixture is then allowed to stir overnight. The mixture is then entered into a separatory funnel and washed with 500 ml of water, 500 ml of HCl (5 percent), 500 ml of water, 500 ml of $NaHCO_3$ (saturated), 500 ml of water, and dried over $MgSO_4$. The mixture is then checked by HPLC &o determine the relative purity of the monomer produced. The methylene chloride is removed via rotary evaporation and the resultant off-white solid is recrystallized from 600 ml of acetone. The first crop of white crystals is removed from solution via filtration and the solution remaining is concentrated to 250 ml and again recrystallized. The second crop of crystals is also isolated via filtration and the remaining solvent is removed to leave a light brown residue. Final weights and purity (by HPLC) are as follows: first crop, 42.10 g, 99.8 percent; second crop, 6.07 g, 99.3 percent; residue, 6.6 g. Yield is 88 percent of theoretical.

EXAMPLE 13

Preparation Of Monomers Corresponding To The Formula

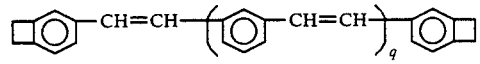

(a) q=3

A 25-ml flask equipped with a reflux condenser, nitrogen inlet, and magnetic stirring bar is charged with m-dibromobenzene (1.0 g, 4.2×10⁻³ m), m-divinylbenzene (2.75 g, 2.1×10⁻² m), tri-n-butylamine (8.4×10⁻³ m), tri-o-tolylphosphine (64 mg, 2.1×10⁻⁴ m), palladium (II) acetate (20 mg, 8.4×10⁻⁵ m), and acetonitrile (10 ml). The mixture is stirred under nitrogen and heated to reflux for 2 hours. The grey slurry is cooled to room temperature and stirred into 60 ml of 10 percent hydrogen chloride The resulting precipitate is collected by filtration, washed with water, and air dried. This product is dissolved in ethylacetate, filtered, and the solvent evaporated to yield a yellow residue. Recrystallization of the residue from heptane gives 0.60 g (42 percent yield) of a compound of the formula

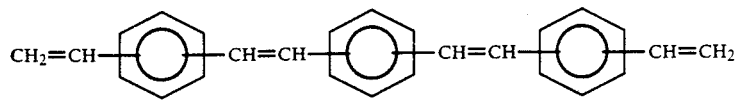

hereinafter referred to as determinal olefin, with a melting point of 105° C.

A 25-ml flask equipped with a reflux condenser, nitrogen inlet and magnetic stirring bar is charged with 4-bromobenzocyclobutene (1.5 g, $8 \times 10^{-3}$ moles), the diterminal olefin from part A (1.34 g, $4 \times 10^{-3}$ moles), tri-n-butylamine (1.8 g, $9.7 \times 10^{-3}$ moles), tri-o-tolylphosphine (62 mg, $4.0 \times 10^{-4}$ moles), palladium II acetate (18 mg, $8.0 \times 10^{-5}$ moles) and acetonitrile (5 ml). The reaction mixture is heated to reflux under nitrogen for 4 hours. The mixture is cooled to room temperature and stirred into 60 ml of 10 percent hydrochloric acid. The precipitate is collected by filtration, washed with water and air dried. The dried precipitate is then dissolved in 150 ml of boiling toluene, filtered hot and cooled to yield 310 mg of the product q=3. The monomer has a melting point of 180° C.–215° C.

(b) q=1

A 25-ml flask equipped with a reflux condenser, nitrogen inlet, and magnetic stirring bar is charged with 4-bromobenzocyclobutene (1.50 g, $8.0 \times 10^{-3}$ m) m-divinylbenzene ($4.0 \times 10^{-3}$ m), tri-n-butylamine (1.8 g, $9.7 \times 10^{-3}$ m), tri-o-tolylphosphine (62 mg, $4.0 \times 10^{-4}$ m), palladium (II) acetate (18 mg, $8.0 \times 1.-^{-5}$ m), and acetonitrile (5 ml). The reaction mixture is heated to reflux under nitrogen with stirring for 4 hours. The solidified mixture is cooled to room temperature and stirred into 60 ml of 10 percent hydrogen chloride. The resulting precipitate is collected by filtration, washed with water, and air dried.

The precipitate is dissolved in 75 ml of boiling ethylacetate, filtered hot, and cooled to yield 800 mg (60 percent of the desired monomer with a melting point of 150° C.–152° C.

EXAMPLE 14

The monomers prepared in Example 10 are tested for melting temperature and polymerization temperature as indicated by the onset and peak exotherm temperature as measured by differential scanning colorimetry (DSC).

The results are in the following table:

| n | Monomer Melting Point (°C.) | Polymerization Temperature (°C.) | |
|---|---|---|---|
| | | DSC Onset | DSC Peak |
| 2 | >245 | 195 | 209 |
| 3 | 121 | 175 | 202 |
| 4 | 173 | 182 | 203 |
| 5 | 60 | 189 | 213 |
| 6 | 157 | 185 | 213 |
| 7 | 61 | 183 | 214 |
| 8 | 171 | overlaps M.P. | 206 |

For melt polymerization it is preferable that the monomer melt at a much lower temperature than that at which it polymerizes and that polymerization occurs by elevating the temperature of the melt. For that purpose, the monomers where n is an odd number are preferred.

The temperature at which polymerization begins and the maximum temperature of polymerization are relatively unaffected by the size of n. The polymers show comparable thermal stability at 400° C.

EXAMPLE 15

Polymerization Of Monomer Prepared By Process Of Example 10 (g)

Into a 10-ml, round-bottom flask connected to a vacuum line is placed 2.5 g of the powdered monomer of Example 10 (g). The flask is evacuated and is immersed in a Woods metal bath at 90° C. The temperature is slowly raised to 250° C over one hour and is held at that temperature for 15 minutes. The flask is then cooled and broken open to remove the solid block of polymer.

EXAMPLE 16

Preparation Of A Coating Using Monomer Of Example 10 (g)

One gram of the monomer of Example 10 (g) is dissolved in 15 ml of N,N-dimethylformamide and is coated on Bonderite 1000 treated steel panels with a 0.010 inch draw bar. The panels are then air dried at room temperature for 1½ hours. Final traces of solvent are removed by heating in a vacuum oven at 70° C. for one hour. The monomer coated plates are then heated in an air oven at 250° C. for one hour to effect polymerization. The polymer coating is brown, glossy, flexible and exhibits a Knoop hardness of 37.

EXAMPLE 17

When the monomers prepared in Example 11 are tested according to the procedures of Example 14, the following results are obtained.

| n | Monomer Melting Point (°C.) | Polymerization Temperature (°C.) | |
|---|---|---|---|
| | | DSC Onset | DSC Peak |
| 3 | 175 | 240 | 271 |
| 5 | 181 | 241 | 271 |
| 6 | 187 | 240 | 271 |
| 7 | 142 | 240 | 272 |
| 8 | 174 | 239 | 272 |

EXAMPLE 18

Polymerization Of Benzocyclobutene/Bisphenol A Ester Monomer

The monomer is devolatilized at 100° C. and 0.5 mm Hg vacuum for two hours, cooled and the vacuum is backlet with nitrogen. The devolatilized monomer (0.5 g) is then transferred to a test tube with a ground glass joint, and equipped with a gas inlet tube topped with T and mineral oil bubbler for nitrogen blanket. The test tube is then placed in a Woods metal bath at 100° C. and slowly taken up to 250° C. The temperature of the Woods metal bath is held at between 245° C.–250° C. for 90 minutes. At the end of this time the test tube is removed from the bath and allowed to cool, still under nitrogen blanket. When cool to the touch, the gas inlet tube is removed and the polymer that remains in the tube is examined. The piece is light yellow in color, contains some voids, and cannot be fractured with a spatula to remove it from the tube.

EXAMPLE 19

The following monomers are tested according to the procedure of Example 14. The results are compiled in Table III.

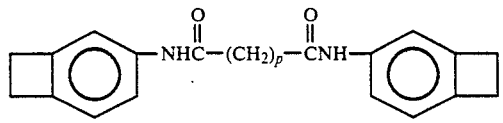

Monomer A

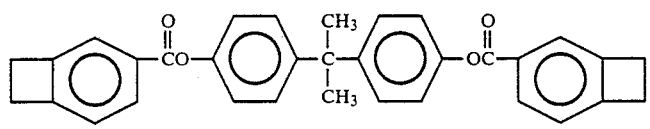

Monomer B

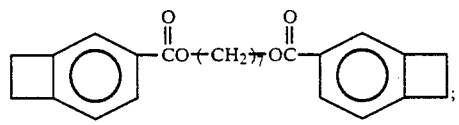

Monomer C

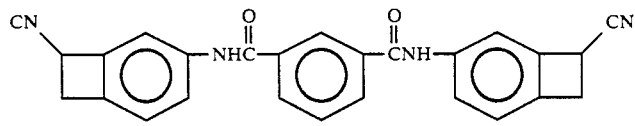

Monomer D

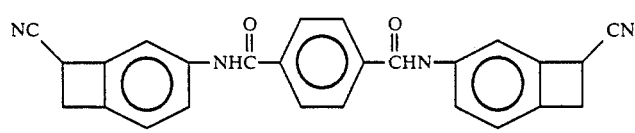

Monomer E

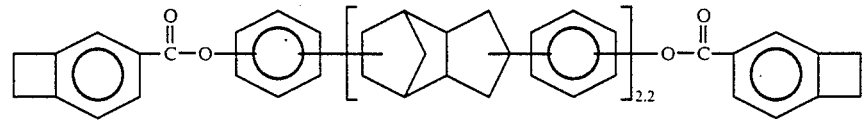

Monomer F

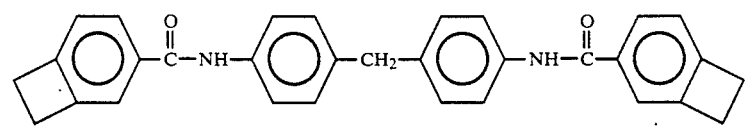

Monomer G

TABLE III

| Monomer | Melting Point | Polymerization Temperature (°C.) | |
|---|---|---|---|
| | | DSC Onset | DSC Peak |
| Series A | | | |
| p = 5 | 161–163 | 200 | 270[1] |
| p = 7 | 163–165 | 200 | 270[1] |
| p = 8 | 174–177 | 200 | 270[1] |
| B | 137 | 200 | 260[2] |
| C | 83 | 200 | 260[2] |
| D* | none | | complex |
| E* | none | | complex |
| F | 67–78 | 200 | 261[2] |
| G | 224 | 200 | 260[2] |

*No melting point observed. A complex differential scanning colorimetry exotherm was observed.
[1]Heating rate 20° C./minute.
[2]Heating rate 10° C./minute.

EXAMPLE 20

Melt Polymerization of Monomer Prepared By Method Described In Example 11 (d)

A mold with a brass cylinder of dimensions 2 ⅛ inch diameter, length 6 inches, 0.313 bore which has one end fitted with a loading head, has a movable piston in the bore and heating bands on the mold, is first coated with a mold release agent. The liquid monomer i(7.15 g) is melted into the mold at 165° C. The mold plus the monomer is cooled to room temperature. The loading head is replaced by a valve head which is attached to the mold and the mold is thereafter purged with nitrogen and heated to 165° C. The gas phase is expelled, the valve head is closed and the liquid monomer is put under pressure of 1290 psi. The mold temperature is raised to 200° C. for 5 minutes, thereafter to 225° C. for 10 minutes, thereafter to 240° C. for 20 minutes, and thereafter to 250° C. for 3 hours. The mold is cooled in 50° increments. At 35° C. the pressure is released on the piston. The product is a rod of finished polymer which is 4.5 inches long and 0.313 inch in diameter which is clear yellow in color.

The polymer prepared in this example demonstrates a 5 percent weight loss at 300° C. after 50 hours in nitrogen. It further demonstrates a hardness of SHORE D equals 90. The tensile strength is 12,000 psi at room temperature and 5,000 to 7,000 psi at 150° C., and it demonstrates a 5 percent elongation at break at 150° C. The rod shows a tensile modulus of $4.7 \times 10^5$ at ( room temperature and $2.2 \times 10^5$ at 200° C. The thermal coefficient of expansion of the rod is, at 25° C. to 250° C., $4.14 \times 10^{-5}$ inch per inch per ° C., and from 250° C. to 325° C., $9.8 \times 10^{-5}$ inch per inch per ° C. The rod has a density of 1.16 g per cm². The rod is subjected to cyclical stress of 2500 to 3000 psi at 150° C. for 250 cycles and there is no evidence of failure.

EXAMPLE 21

Melt Polymerization Of Monomer B From Example 19

The same molding equipment as described in Example 19, is loaded with 6.72 g of monomer B at 165° C. The mold temperature is raised to 180° C. and the valve head is closed. The mold temperature is raised to 190° C. and the monomer is put under pressure of 2410 psi. The mold temperature thereafter was raised to 250° C. in 10° increments wherein each temperature was held for 10 minutes. Thereafter the mold was held at a temperature of 250° C. for 3 hours. The mold is cooled to below 35° C. in 25° C. increments, each temperature increment is held for 10 to 15 minutes. The valve head is removed and a polymer rod with a length of 4.25 inches and 5/16 diameter which is translucent and yellow in color results. The polymer demonstrates a 5 percent weight loss after 65 hours in air at 300° C. A water absorption test demonstrates a 0.35 weight percent pickup after 24 hours in water at 25° C. Further, a water pickup of 1.5 weight percent after 96 hours in water at 95° C. is shown. The thermal coefficient of expansion from 25° C. to 325° C. is $5.2 \times 10^{-5}$ inches per inch per ° C.

EXAMPLE 22

Preparation Of Film From The Monomer Prepared By Process Described In Example 10 (g)

A monomer (0.5 g) prepared by the method described in Example 10 (g) is dissolved in 2 ml of dimethyl sulfoxide. The solution is coated onto aluminum plates with a 0.010 inch draw bar. The plate is placed in an air oven at 250° C. for one hour. The polymer coating which is formed is smooth, glossy, dark amber in color, has a Knoop hardness of 34 and the plate can be bent 90° without cracking the coating. The coating is only slightly swollen by immersion in dimethyl sulfoxide overnight. The coating is mechanically peeled off of one aluminum plate to give a flexible film of 0.001 inch thickness. The film has a tensile strength of 12,000 psi at room temperature and a 5 percent elongation at break. The tensile modulus is 350,000. The film demonstrates no failure after cycling it under 6,000 to 8,000 psi load for 100 cycles at room temperature.

EXAMPLE 23

Use Of Monomer Prepared By The Method Described In Example 11 (d) As An Adhesive A one-inch square on the end of a steel coupon of 4 inches by 1 inch by 0.060 thickness is covered with powdered monomer prepared by the method described in Example 11 (d). This is overlapped with a second coupon of the same size. A one-inch square of the second coupon's end is covered with a powdered monomer and this is overlapped with a third coupon of the same size. These coupons are overlapped in a manner such that there is a one-inch square of each in contact with one of the others wherein powdered monomer is between the overlapped plates. A weight is placed on the joint and the plates are thereafter heated in an air oven at 250° C, for 1.5 hours. Thereafter the lap shear force needed to pull the coupons apart is measured. Table IV demonstrates the joint thickness and lap shear of six such adhesivated coupons.

TABLE IV

| Sample | weight* (lb) | average joint thickness (inches) | lap shear (lb) |
|---|---|---|---|
| 1 | 1 | 0.0075 | 4,600 |
| 2 | 1 | 0.0085 | 3,000 |
| 3 | 1 | 0.0075 | 3,100 |
| 4 | 7 | 0.006 | 2,900 |
| 5 | 7 | 0.005 | 3,300 |
| 6 | 7 | 0.004 | 3,700 |

*Weight on joint during curing.

EXAMPLE 24

Formation Of Prepolymer From Monomer Prepared By Method Described In Example 11 (d)

Under vacuum 8.3 g of the monomer prepared by the process described in Example 11 (d) is devolatilized. The monomer is thereafter heated under nitrogen at 200° C. for 10 minutes, and then at 220° C. for 16 minutes. The monomer is cooled to room temperature. The prepolymer is a yellow glass, which is thereafter broken up into a powder.

EXAMPLE 25

Compression Molding Of Prepolymer From Example 24

A rectangular compression mold ($1.9 \times 10.2$ cm) is coated with a mold release agent. Into the mold is placed 6.3 g of the powdered prepolymer from Example 23. The mold is closed and placed in press. Thirteen hundred pounds of pressure is applied and the mold is heated to 200° C. The pressure is increased to 20,000 pounds and the mold temperature is raised to 230° C. Thereafter the mold is heated to 240° C. over a 30-minute period and held at such temperature for one hour. Thereafter the mold is cooled to room temperature.

The molded polymer is yellow brown in color and translucent. It has a density of 1.16 g per cm³ and a hardness of 90 (shore d). The polymer has a tensile strength of 3800 psi at 20° C. and a tensile modulus of $3.8 \times 10^5$. The elongation at break is 5 percent and the coefficient of thermal expansion from 20° C. to 200° C. is $4.9 \times 10^{-5}$. The water pickup at 100° C. is about 3 weight percent.

EXAMPLE 26

Preparation Of Prepolymer By Precipitation Polymerization Of Monomer Prepared By Method Of Example 11 (d)

Biphenyl (50 g) is melted and heated to 100° C under nitrogen. To the solution is added 2.0 g of the monomer prepared by the process described in Example 11 (d). The mixture is heated to 230° C. and held for 5.5 hours. During this time, the prepolymer precipitates out of solution. The reaction mixture is cooled to room temperature, and thereafter warmed slightly to liquefy the biphenyl. Toluene is added and the prepolymer is filtered off. The prepolymer is thereafter washed with toluene and dried under vacuum.

EXAMPLE 27

Polymerization Of Prepolymer Prepared In Example 26

A mold which is a steel cylinder with a 0.5 inch diameter bore with two flat pistons that match the bore is used in this example. The mold and pistons are treated with a mold release agent. One piston is placed into the mold and 0.5 g of prepolymer is added. The second piston is placed on top of the monomer and the assembly placed in a press. Pressure (7.5 tons) is applied to the pistons. The mold is heated to 170° C. Thereafter the pressure is increased to 10 tons and the temperature is held at 170° C. for 30 minutes. Thereafter the temperature is raised to 250° C. and held for 2 hours. The mold is thereafter cooled and the polymer disc is removed.

The polymers prepared in this method are amber and translucent. The polymer disc exhibits a 4 percent weight loss at 400° C. in nitrogen. The coefficient of thermal expansion of the polymer is $1 \times 10^{-4}$ inch per inch per ° C. from 25° C. to 125° C.; from 125° C. to 225° C. $20 \times 10^{-4}$ inch per inch per ° C.; and from 225° C. to 300° C. $3 \times 10^{-4}$ inch per inch per ° C.

EXAMPLE 28

Solution Polymerization Of The Monomer Prepared By the process Described In Example 11 (d)

In 10 ml of N-methyl-2-pyrrolidinone is dissolved 2.0 g of monomer. To this solution is added 0.5 g of lithium chloride. The mixture is stirred and refluxed under nitrogen for 5 hours. Thereafter the solution is cooled to room temperature and into the mixture is poured 250 ml of water. The polymer precipitates upon addition of the water. The polymer is filtered off and vacuum dried at 150° C.

EXAMPLE 29

Solid State Polymerization Of Monomer (d) From Example 19

One gram of the solid monomer (d) as described in Example 18 is placed in a flask, the monomer is heated to 250° C. under vacuum and held there for ½ hour. The polymer prepared is thereafter cooled to room temperature. The resultant polymer is a powder.

EXAMPLE 30

Preparation Of A Divinylsiloxane Bis-benzocyclobutene Monomer

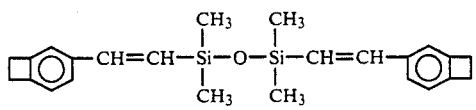

In a 500 ml flask equipped with a reflux condenser and magnetic stirrer is placed 50.0 g (0.273 moles) of 4-bromobenzocyclobutene, 25.4 g (0.136 moles) of 1,3-divinyl-1,1,3,3 tetramethyl disiloxane, 0.613 g (0.0027 moles) of palladium II acetate, 1.66 g (0.0055 moles) of tri-0-tolylphosphine, 30.3 g (0.300 moles) of triethylamine and 150 ml of acetonitrile. The mixture is stirred and heated to reflux under nitrogen for 20 hours. It is then cooled to room temperature and treated with a mixture of methylene chloride (500 ml) and water (200 ml). The methylene chloride layer is separated and vigorously stirred with 200 ml of 10 percent aqueous hydrogen peroxide at room temperature for four hours. The methylene chloride layer is separated and extracted with 200 ml of H₂O. The methylene chloride layer is then dried over anhydrous magnesium sulfate, filtered and concentrated under vacuum. The crude product is treated with 150 ml of heptane and allowed to stand at room temperature overnight. The mixture is then filtered to remove the solid impurity which crystallized out. The filtrate is concentrated under vacuum and then subjected to Kugelrohr distillation (160° C., 1 mm) to remove volatile impurities. The resulting product is then chromatographed over silica gel using two percent ethyl acetate in heptane as an eluent. The fractions containing the product are combined and concentrated to give 35.5 g of divinylsiloxane bis-benzocyclobutene monomer as a colorless oil.

EXAMPLE 31

Preparation Of A Divinylsilane Bis-benzocyclobutene Monomer

In a 50 ml flask equipped with a reflux condenser and magnetic stirrer is placed 6.00 g (0.033 moles) of 4-bromobenzocyclobutene, 1.84 g (0.016 moles) of divinyl dimethylsilane, 0.074 g (0.0003 moles) of palladium II acetate, 0.20 g (0.0007 moles) of tri-0-tolylphosphine, 3.98 g (0.039 moles) of triethylamine and 20 ml of acetonitrile. The mixture is then stirred and heated at reflux under nitrogen for 16 hours. The mixture is then cooled to room temperature and treated with a mixture of methylene chloride (100 ml) and H₂O (50 ml). The methylene chloride layer is then separated and vigorously stirred with 50 ml of 10 percent aqueous hydrogen peroxide at room temperature for two hours. The methylene chloride layer is separated, extracted once with 50 ml of water, and finally dried over anhydrous magnesium sulfate. The magnesium sulfate is removed by filtration and the filtrate is concentrated under vacuum to give the crude monomer. This is then chromatographed over basic alumina using 10 percent ethyl acetate in heptane as the eluent. The appropriate fractions are collected and concentrated under vacuum to give 2.5 g of a solid/oil mixture. This is then washed with three two ml portions of heptane. The combined heptane washes are combined and concentrated under vacuum to give 0.90 g of the divinylsilane bis-benzocyclobutene as a colorless oil.

EXAMPLE 32

Preparation Of A Divinylsilylethylene Bis-benzocyclobutene Monomer

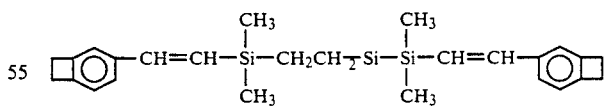

In a 50 ml flask equipped with a reflux condenser and magnetic stirrer is placed 6.00 g (0.033 moles) of 4-bromobenzocyclobutene, 3.26 g (0.016 moles) of 1,4-divinyl-1,1,4,4 tetramethyl disilylethylene, 0.074 g (0.0003 moles) of palladium II acetate, 0.20 g (0.0007 moles) of tri-0-tolylphosphine, 3.98 g (0.039 moles) of triethylamine, and 20 ml of acetonitrile. The mixture is stirred and heated to reflux under nitrogen for four hours. The mixture is cooled to room temperature and treated with a mixture of methylene chloride (200 ml) and H₂O (100 ml). The methylene chloride layer is separated and vigorously stirred with 00 ml of 10 percent aqueous hydrogen peroxide at room temperature The solvent is then removed under vacuum to yield the amic acid which corresponds to the formula

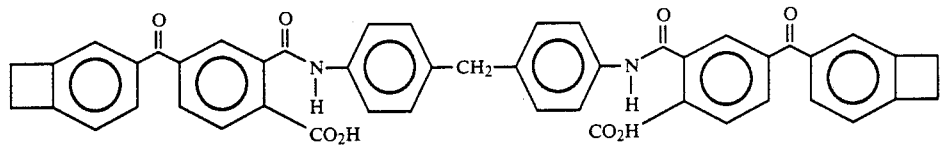

for two hours. The methylene chloride layer is separated, extracted once with $H_2O$, and dried over anhydrous magnesium sulfate. The magnesium sulfate is filtered off and the filtrate is concentrated under vacuum to give the crude product. This s then chromatographed on silica gel using heptane as the eluent. The appropriate fractions are collected, combined, and concentrated under vacuum to give the product. This is as a bright yellow powder. The amic acid is then treated with 10.82 g (0.106 moles) of acetic anhydride and heated at 120° C. under nitrogen for 16 hours. The reaction mixture is cooled to room temperature and the excess acetic anhydride is removed under vacuum. The reaction mixture is then dissolved in 5 ml of tetrahydrofuran and added to 100 ml of vigorously stirred $H_2O$. The yellow product of the formula

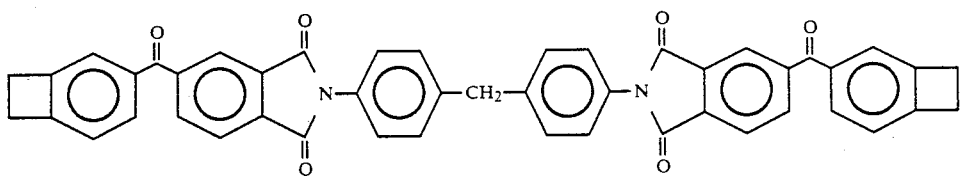

recrystallized from methanol to give 0.83 g of pure material; divinylsilylethylene bis-benzocyclobutene with an M P 83°-84° C.

as a powder is filtered of and dried to yield 0.19 g (61.5% yield) of product.

EXAMPLE 33

Preparation Of A Bis Imide Bis-benzocyclobutene Monomer

EXAMPLE 34

Preparation Of A Bis-benzocyclobutene Of The Formula

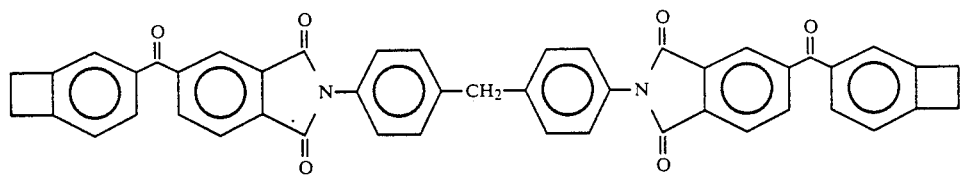

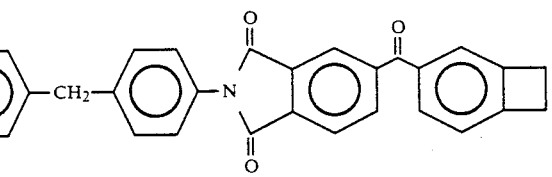

Into a 25 ml flask equipped with a magnetic stirrer and nitrogen bubbler is placed 0.24 g (0.00086 moles) of the keto anhydride corresponding to the formula

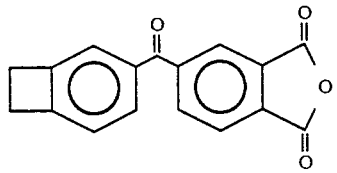

and 5 ml of acetone. (See Example 47 for the preparation of this compound.) This solution is stirred vigorously and 0.085 g (0.00043 moles) of the diamine corresponding to the formula

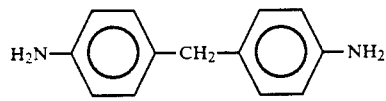

is added in one portion at room temperature. The mixture is then stirred for 30 minutes at room temperature.

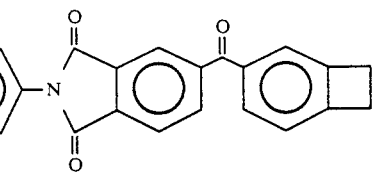

Into a 50 ml flask equipped with a nitrogen bubbler, rubber septum, and magnetic stirrer is placed 1.92 g (0.0082 moles) of 4,4' dimercaptodiphenyl ether and 20 ml of tetrahydrofuran. This is stirred at room temperature and 0.400 g (0.0165 moles) of sodium hydride is added in small portions. The resulting slurry is then stirred at room temperature for 60 minutes. In a second flask that is equipped with a nitrogen bubbler, rubber septum, reflux condenser, and magnetic stirrer is placed 3.0 g (0.016 moles) of 4-bromobenzocyclobutene. To this is added 30 ml of toluene and 0.945 g (0.0008 moles) of tetrakis triphenylphosphine palladium (0). This mixture is stirred and heated at reflux under nitrogen for 60 minutes. To this hot mixture is o then added the 4,4'dimercaptodiphenyl ether sodium hydride mixture. The combined mixtures are then stirred and heated at reflux under nitrogen for 16 hours. The mixture is then cooled to room temperature and treated with 20 ml of $H_2O$ and 100 ml of toluene. The toluene layer is separated and saved. The aqueous layer is then extracted with 100 ml of toluene and this extract is combined with the first toluene extract. The combined toluene extracts are then washed with three 50 ml portions of H₂O and dried over anhydrous magnesium sulfate. The mixture is filtered and the filtrate is concentrated under vacuum to yield the crude product as a pale yellow oil. This is purified by chromatography over silica gel using 10 percent ethyl acetate in heptane as the eluent. The appropriate fractions were collected and concentrated under vacuum to give a solid monomer corresponding to the formula

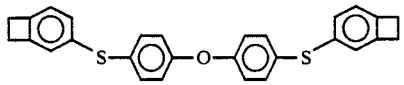

M.P. 79°-80° C.

EXAMPLE 35

Preparation Of Bis-benzocyclobutene Monomer Of The Formula

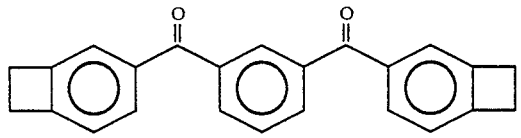

In a 50 ml three neck flask equipped with a nitrogen bubbler, rubber septum, and magnetic stirrer is placed 1.46 g (0.0072 moles) of isophthaloyl chloride and 10 ml of nitrobenzene. To this is then added 3.88 g (0.0129 moles) of antimony pentachloride. The mixture is then stirred under nitrogen at room temperature for 20 minutes. It is then cooled to −25° C. at which point the mixture solidifies. To this solid mixture is added a solution 1.50 g (0.0144 moles) of benzocyclobutene in 5 ml of nitrobenzene. The mixture is then warmed to −5° C. and held at this temperature for two hours. Next, 3 ml of ethanol is added to the mixture and it is warmed to room temperature. It is then poured into 100 ml of H₂O and extracted with two 100 ml portions of toluene. The toluene extracts are combined and extracted successively with H₂O, brine, 10 percent aqueous sodium hydroxide, and finally, H₂O. The toluene extract is then dried over anhydrous magnesium sulfate, filtered and concentrated under vacuum to give a dark oil. This oil is subjected to steam distillation until all of the nitrobenzene is removed. The residue is taken up in toluene and dried over anhydrous magnesium sulfate. It is filtered and concentrated under vacuum to yield an oil which upon treatment with 2 ml of ethanol solidifies. The product ethanol mixture is dried under vacuum and the solid product recrystallizes from a mixture of ethanol and ethyl acetate to yield the pure diketone monomer of the formula

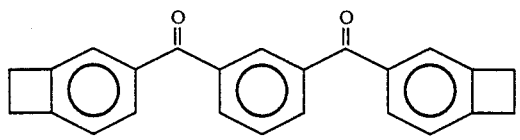

M.P. 138°-139° C.

EXAMPLE 36

PreparaTion Of A Bis-benzocyclobutene Monomer Of The Formula

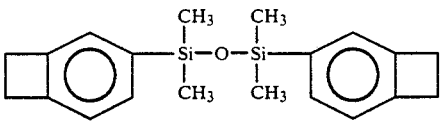

In a 100 ml three neck flask equipped with a nitrogen bubbler, addition funnel, and reflux condenser is placed 1.35 g (0.0055 moles) of magnesium turnings and 5 ml of tetrahydrofuran. To this is added 1.0 g (0.0054 moles) of 4-bromobenzocyclobutene. In the addition funnel is placed 9.1 g (0.0497 moles) of 4-bromobenzocyclobutene and 15 ml of tetrahydrofuran. The mixture in the flask is stirred and heated to reflux under nitrogen. The contents of the addition funnel are added to the refluxing reaction mixture. When the addition is complete, the reaction mixture is stirred and heated at reflux for 45 minutes. A solution of 5.4 g (0.027 moles) of 1,3 dichloro 1,1,3,3 tetramethyldisiloxane in a 20 ml of tetrahydrofuran is placed in the addition funnel and slowly added to the refluxing reaction mixture. After three hours, an additional 0.50 g (0.002 moles) of 1,3 dichloro 1,1,3,3 tetramethyldisiloxane is added, and after 3.75 hours, another 0.40 g of 1,3 dichloro 1,1,3,3 tetramethyldisiloxane is added. Following this last addition, the reaction mixture is refluxed for another 15 minutes and then cooled to room temperature. The mixture is treated with 5 ml of saturated aqueous ammonium chloride and 0 ml of tetrahydrofuran. Another 50 ml of tetrahydrofuran is added followed by anhydrous magnesium sulfate. The mixture is filtered and the filtrate concentrated to yield 12 g of an amber oil. The oil is chromatographed on silica gel using pentane as the eluent to yield 1.2 g of monomer of the formula

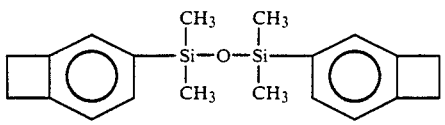

as a colorless oil.

EXAMPLE 37

Preparation Of A Bis-benzocyclobutene Monomer Of The Formula

A 500 ml three neck flask is equipped with an overhead stirrer, nitrogen bubbler, and a gas dispersion tube. A solution of 4.169 g (0.012 moles) of 1,3 di[2-(4-benzocyclobutenyl)ethenyl]benzene in 350 ml of toluene is placed in the flask. Next 0.40 g of five percent palladium on carbon catalyst is added and the mixture is purged by bubbling nitrogen through the gas dispersion tube. After 15 minutes, the nitrogen flow is turned off and replaced by a stream of hydrogen gas. The hydrogen gas is bubbled through the reaction mixture until the hydrogenation is complete as evidenced by sampling the mixture and analyzing by liquid chromatography.

When the reaction is complete, the mixture is again purged with nitrogen and the catalyst is filtered off. The filtrate is concentrated under vacuum to give a solid product of the formula

which is recrystallized two times from ethanol to give 2.1382 g of such monomer with a melting point of 91° C.

EXAMPLE 38

Preparation Of

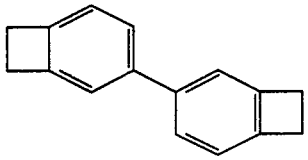

A Grignard reagent is prepared in a 50 ml three neck round bottom flask equipped with a mechanical stirrer, a reflux condenser with a gas inlet adapter and a positive nitrogen flow supplied via a mineral oil bubbler, and an addition funnel. The apparatus is thoroughly dried with a heat gun while being purged with dry nitrogen. 0.139 g Mg (A.W.=24.3 g, 0.00573 g-atoms) is added to this flask, and the apparatus is again dried with a heat gun. Five ml dry Tetrahydrofuran (THF) is then added to the flask, and 0.5 g 4-bromobenzocyclobutene is added to the mixture with vigorous stirring. The flask is then equipped with a heating mantle and a thermocouple. When the Grignard reagent begins to form (as evidenced by a darkening of the solution and the temperature rising above 50° C.), another 0.5 g 4-bromobenzocyclobutene (M.W.=183.05, total addition of 4-bromobenzocyclobutene 1.0 g, 5.46 mmoles) in 15 ml dry THF is added quickly via the addition funnel. The mixture is then refluxed for 60 minutes.

Another apparatus consisting of a 100 ml three neck round bottom equipped with a reflux condenser with a gas inlet adapter, a positive pressure nitrogen supplied via a mineral oil bubbler, an addition funnel, and a stopper is assembled and dried with a heat gun. To this apparatus is added 2.208 g TlBr (M.W.=284.28, 7.7 moles) and 20 ml toluene. This flask is then equipped with magnetic stirring and a heating mantle with a high temperature shut-off device. The already formed Grignard reagent is then transferred through a cannula to the addition funnel on the 100 ml flask, and is added to the stirred TlBr/toluene mixture. Another 5 ml of dry THF is added to the Grignard flask and washed through the cannula and addition funnel into the reaction flask. The solution turned dark upon addition of the Grignard solution. The solution is then refluxed overnight.

The reaction is worked up by pouring the contents of the flask into 200 ml H$_2$O and extracting the product into two 100 ml aliquots of methylene chloride. The combined extracts are washed with 100 ml H$_2$O, 100 ml five percent aqueous HCl, 100 ml H$_2$O, 100 ml sat'd NaHCO$_3$, 100 ml H$_2$O, and dried over MgSO$_4$. This methylene chloride is then removed via rotary evaporation, and the slightly orange oil is taken up in 50 ml hexane and filtered through a short column of alumina (to remove any unreacted organothallium salts.) The resultant clear solution is analyzed by thin layer chromatography (silica gel plates, 9:1 petroleum ether: methylene chloride eluent) and two spots, one at Rf=0.5, and a smaller one at Rf=0.4. Recrystallization from pentane gives 0.18 g 4,4'-bisbenzocyclobutene which is pure by analysis. This represents a 32% yield; the mother liquor contains a substantial amount of the product, but further purification of this mixture is not attempted. IR (KBr) 2960, 2920, 1460, 880, 820 cm$^{-1}$. H'NMR (CDCl) 3.1 (s, 4H). 6.93–7.4 (m, 3H). Elemental analysis-carbon, 93.2%, hydrogen, 6.86%, theoretical carbon content, 93.16%, hydrogen, 6.84%, melting point 64°–66° C.

EXAMPLE 39

Preparation Of 1,3-(Bis(4-benzocyclobutenyl))-benzene

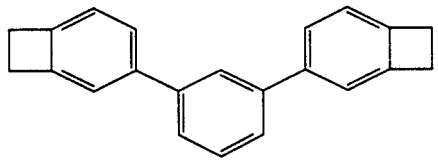

A 100 ml three neck flask is equipped with a mechanical stirrer, a reflux condenser with positive nitrogen pressure via a mineral oil bubbler, and an addition funnel. The apparatus is carefully dried with a heat gun while nitrogen is blown through the flask. To the flask is added 0.133 g Mg (A.W.=24.3 g, 0.00546 g-atoms) and this is also dried with a heat gun. To this is added enough dry THF to cover the Mg, and 0.5 g 4-bromobenzocyclobutene is added directly to the flask. The solution is then heated with a heat gun until the THF begins to reflux, and when the solution begins to darken and maintain an elevated temperature (ca. 50° C.) without external heat, another 0.5 g 4-bromobenzocyclobutene is added (total addition 1.0 g, or 0.00546 mmoles). The reaction mixture is then refluxed for 30 minutes.

Another apparatus is used to carry out the coupling reaction. This reaction is run in a 50 ml two neck flask equipped with an addition funnel, a reflux condenser with a gas inlet tube, and a positive nitrogen pressure supplied via a mineral oil bubbler, and magnetic stirring. To the dried apparatus is added 0.315 g Pd(PPn )4 (M.W.=1155.6 g, 0.273 moles, or 5 mole percent), 10 ml THF, and 0.64 gm-dibromobenzene (M.W.235.92, 2.73 mmoles). The Grignard reagent is then added dropwise the stirring reaction mixture. The Grignard flask is washed with 5 ml of dry THF, and this solution is washed and into the reaction flask. The reaction is then heated to reflux, and this condition is maintained overnight.

The reaction is worked up by cooling and diluting with 100 ml H$_2$O. The product is then extracted into three 50 ml aliquots of methylene chloride, and the combined extracts are washed with 100 ml 5% aqueous HCl, 100 ml H$_2$O and dried over MgSO$_4$. The methylene chloride is then removed via rotary evaporation, and analysis via TLC (silica gel plate, petroleum ether eluent) gives two spots, one a Rf=0.4, and another, smaller spot at Rf=0.6. The pure compound is isolated initially by flash chromatography (petroleum ether eluent flash chromatography grade 230–400 mesh silica gel). The pure 1,3-(bis(4-benzocyclobutenyl))benzene melts at 94°–96° C. The rest of the compound is purified via recrystallization from hexane. The total yield of product is 0.57 g, or 72.0% of theory. IR(KBr) 2960, 2920, 1600, 1460, 1420, 1250, 1218, 890, 875, cm$^{-1}$. Elemental analysis gives 93.58% carbon, 6.42% Hydrogen.

EXAMPLE 40

Polymerization Of Monomers Of Example 33

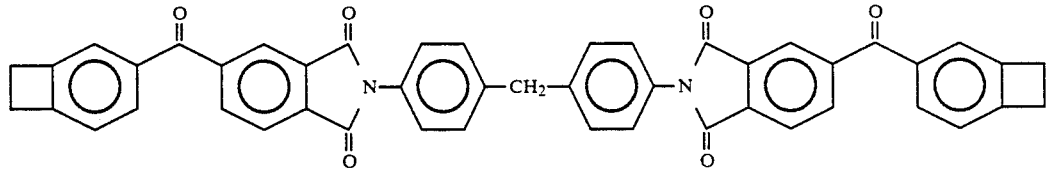

A 0.15 g sample of the compound prepared as described in Example 33 is placed on a microscope slide and slowly heated to 250° C. At 150° C., the monomer is completely molten and flows out to give a film. At 250° C., the fluid film hardens as the monomer polymerizes. The sample is cooled to room temperature and the film is peeled off the glass. The film is immersed in one molar aqueous potassium hydroxide and shows no swelling or softening.

EXAMPLE 41

Polymerization Of Monomer Of Example 34

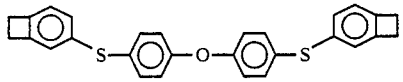

A 0.120 g sample of a monomer prepared in Example 34 is placed in a test tube and heated to 270°60 C. under a nitrogen atmosphere using the time/temperature schedule shown below.

| TEMPERATURE °C. | TIME AT TEMPERATURE (minutes) |
|---|---|
| 200 | 30 |
| 210 | 30 |
| 220 | 60 |
| 235 | 60 |
| 250 | 120 |
| 270 | 60 |

The sample is cooled to room temperature and the solid piece of polymer is removed. The polymer was analyzed by thermogravimetric analysis (TGA) and found to have a one percent weight loss at 385°60 C.

EXAMPLE 42

Polymerization Of Monomers Of Example 33

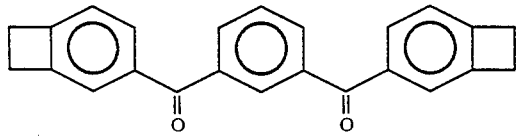

A 0.100 g sample of the monomer prepared as described in Example 35 is placed in a test tube and heated to 270° C. under a nitrogen atmosphere using the time/-temperature schedule shown below.

| TEMPERATURE °C. | TIME AT TEMPERATURE (minutes) |
|---|---|
| 200 | 30 |
| 220 | 30 |
| 235 | 30 |
| 250 | 60 |
| 270 | 60 |

The sample is cooled to room temperature and the solid polymer removed and examined by thermogravimetric analysis (TGA). It shows a one percent weight loss at 375° C. under nitrogen.

EXAMPLE 43

Polymerization Of Monomer Of Example 36

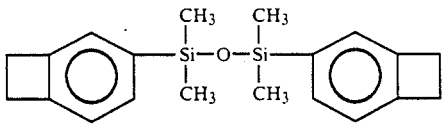

A 0.200 g sample of the monomer prepared as described in Example 36 is placed in a test tube and heated to 270° C. under a nitrogen atmosphere using the heating schedule shown below.

| TEMPERATURE °C. | TIME AT TEMPERATURE (minutes) |
|---|---|
| 200 | 30 |
| 210 | 30 |
| 220 | 60 |
| 235 | 60 |
| 250 | 120 |
| 270 | 60 |

The sample is cooled to room temperature and the solid polymer is removed and examined by thermogravimetric analysis (TGA). It shows a one percent weight loss at 419° C. under nitrogen.

EXAMPLE 44

Polymerization Of Monomer Of Example 37

A 0.100 sample of a monomer prepared as described in Example 37 is placed in a test tube and blanketed with a nitrogen atmosphere. It is then placed in a heating bath at 175° C. and held at that temperature for 15 minutes. It is then heated to 200° C. and held for 25 minutes, then to 220° C. and held for 25 minutes, and finally to 240° C. and held for 20 minutes. The tube is cooled to room temperature and the piece of solid polymer removed. It showed a two percent weight loss at 419° C. by thermogravimetric analysis (TGA) under nitrogen.

EXAMPLE 45

Polymerization Of Monomer Of Example 38 4,4'-Bisbenzocyclobutene

A polymerization tube with an inner diameter of 1/5 inch and 9 inches long is loaded with 100 mg of purified 4,4'bisbenzocyclobutene. This is then melted in a Wood's metal bath under dry nitrogen at 100° C., and the temperature is raised to 250° C. over a 90 minute period. This temperature is then held at 250° C. for two hours, and the sample is removed from the bath and allowed to cool to room temperature. The glass tube is carefully broken away to leave a slightly orange-yellow polymer piece, weighing 100 mg.

EXAMPLE 46

Polymerization of monomer of Example 39 1,3-(bis-(benzocycloebutenyl)benzene

A polymerization tube with an inner diameter of 1/5 inch and 9 inches long is loaded with 100 mg of purified 1,3-(bis-[4-benzocyclobutenyl])benzene. This monomer is then melted in a Wood's metal bath under dry nitrogen at 100° C., and the temperature is raised to 250° C. over a 90 minute period. This temperature is then held at 250° C. for two hours, and the sample is removed from the bath and allowed to cool to room temperature. The glass tube is carefully broken away to leave a slightly orange-yellow polymer piece, weighing 100 mg.

example 47

Preparation of 4-benzocyclobutenyl-4-(1,2-dicarboxylic Acid Anhydrido) Phenyl Ketone

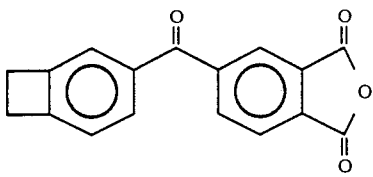

Into a 25 ml round bottom flask, equipped with a magnetic stirring bar, and reflux condenser with a nitrogen inlet is placed 3.0 g (28.85 mmol) of benzocyclobutene, 4.07 g (19.23 mmol; 0.67 eq. per equivalent of benzocyclobutene) of trimellitic anhydride acid chloride, and 31 mg (0.913 mmol) of iron (III) oxide. The flask is placed in an oil bath and the mixture is vigorously stirred at 140° C. for 20 hours. At the end of this time, the deep red-brown reaction mixture is cooled to room temperature and taken up in 100 ml of chloroform and transferred to a separatory funnel. The organic phase is washed with ten percent aqueous sodium bicarbonate (2×50 ml); water (2×50 ml) and saturated aqueous sodium chloride (1×50 ml). The organic layer is dried over magnesium sulfate and then filtered through celite. The resulting solution is concentrated on a rotary evaporator to yield a deep red-brown viscous liquid. The product is treated with n-hexane (100 ml) and vigorously agitated for five minutes. The hexane is decanted away from the insoluble residue and the hexane treatment is repeated two more times. The combined hexane extracts are concentrated on a rotary evaporator and to yield 501 mg of a bright yellow liquid. This liquid is 2-phenethyl chloride. The material which is left behind after the room temperature hexane washes becomes a dark yellow solid. This material is treated with hot hexane (boiling) to provide 1.5 g of a bright yellow solid that is soluble in the hot hexane. The bright yellow product is recrystallized form carbon tetrachloride and a small amount of decolorizing charcoal to provide a bright yellow solid which is 4-benzocyclobutenyl-4-(1,2 dicarboxylic acid anhydrido) phenyl ketone. Yield 1.5 g (28%). Melting point, 131°-132° C. NMR, IR, Elemental analysis, mass spectrum, and DSC of the product is consistent with the structure.

What is claimed is:

1. A poly(arylcyclobutene) which corresponds to the formula

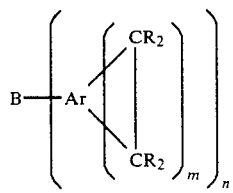

wherein

B is an amidoalkyl terminated polysiloxane, wherein the carbonyl carbon of each amide is bound to Ar;

R is separately in each occurrence hydrogen, an electron-withdrawing substituent or an electron-donating substituent;

Ar is an aromatic moiety or an aromatic moiety substituted with an electron-withdrawing substituent or electron-donating substituent with the proviso that the carbons of the cyclobutene ring

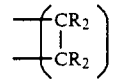

are bonded to adjacent carbon atoms on the same aromatic ring of Ar;

m is an integer of 1 or greater;

n is an integer of 2 or greater; and with the further proviso that the compound be polymerizable through opening of the cyclobutene rings.

2. The poly(arylcyclobutene) of claim 1 wherein Ar is benzene, naphthalene, biphenyl, binaphthyl or a diphenylalkane radical.

3. The poly(arylcyclobutene) of claim 2 wherein Ar is benzene.

4. The poly(arylcyclobutene of claim 3 which corresponds to the formula

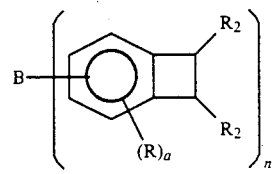

wherein

B is an amidoalkyl terminated polysiloxane, wherein the carbonyl carbon of each amide is bound to the benzene ring;
R is separately in each occurrence hydrogen or an electron-withdrawing substituent or electron-donating substituent;
a is 3;
n is an integer of 2 or greater; and
with the proviso that the poly(arylcyclobutene) be polymerizable through opening of the cyclobutene rings.

5. The poly(arylcyclobutenes) of claim 4 wherein n is 2 or 3.

6. The poly(arylcyclobutenes) of claim 5 wherein n is 2.

7. The poly(arylcyclobutene) of the formula

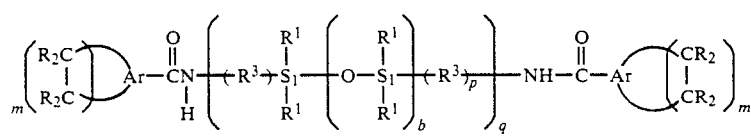

wherein
Ar is an aromatic moiety or an aromatic moiety substituted with an electron withdrawing substituent or electron donating substituent;
m is an integer of 1 or greater;
R is separately in each occurrence hydrogen, an electron-withdrawing substituent or an electron-donating substituent;
$R^1$ is separately in each occurrence an alkyl, aryl, alkaryl, aralkyl, alkoxy, aryloxy, alkaryloxy, or aralkyloxy;
$R^3$ is alkylene;
b is an integer of 1 or greater;
p is 1;
q is 1 or greater; and
with the proviso that the poly(arylcyclobutene) be polymerizable through opening of the cyclobutene rings.

8. The poly(arylcyclobutene) of the formula

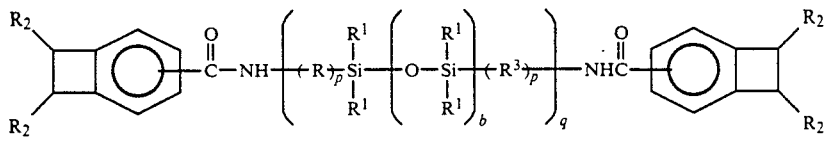

wherein
R is separately in each occurrence hydrogen, an electron-withdrawing substituent or an electron-donating substituent;
$R^1$ is separately in each occurrence an alkyl, aryl, alkaryl, aralkyl, alkoxy, aryloxy, alkaryloxy, or aralkyloxy;
$R^3$ is alkylene;
b is an integer of 1 or greater;
p is 1;
q is 1 or greater; and
with the proviso that the poly(arylcyclobutene) be polymerizable through opening of the cyclobutene rings.

* * * * *